US007446112B2

(12) United States Patent
Grootenhuis et al.

(10) Patent No.: US 7,446,112 B2
(45) Date of Patent: Nov. 4, 2008

(54) MODULATORS OF MUSCARINIC RECEPTORS

(75) Inventors: Peter D. J. Grootenhuis, San Diego, CA (US); Miguel Garcia-Guzman Blanco, San Diego, CA (US); Lewis R. Makings, Encinitas, CA (US); Philip Martin Londo, Santee, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 214 days.

(21) Appl. No.: 11/005,944

(22) Filed: Dec. 7, 2004

(65) Prior Publication Data

US 2005/0171141 A1    Aug. 4, 2005

Related U.S. Application Data

(60) Provisional application No. 60/528,049, filed on Dec. 9, 2003.

(51) Int. Cl.
*A61K 31/4375* (2006.01)
*C07D 471/02* (2006.01)
(52) U.S. Cl. .................................... 514/300; 546/122
(58) Field of Classification Search ................. 514/300; 546/122
See application file for complete search history.

(56) References Cited

U.S. PATENT DOCUMENTS

| | | | |
|---|---|---|---|
| 6,103,903 | A | 8/2000 | Cai et al. |
| 6,166,203 | A | 12/2000 | Cai et al. |
| 6,380,209 | B1 | 4/2002 | Cai et al. |
| 6,596,730 | B1 | 7/2003 | Coulton et al. |
| 6,610,677 | B2 | 8/2003 | Davies et al. |
| 6,613,776 | B2 | 9/2003 | Knegtel et al. |
| 6,638,926 | B2 | 10/2003 | Davies et al. |
| 6,653,300 | B2 | 11/2003 | Bebbington et al. |
| 6,653,301 | B2 | 11/2003 | Bebbington et al. |
| 6,656,939 | B2 | 12/2003 | Bebbington et al. |
| 6,660,731 | B2 | 12/2003 | Bebbington et al. |
| 6,664,247 | B2 | 12/2003 | Bebbington et al. |
| 6,696,452 | B2 | 2/2004 | Davies et al. |
| 6,727,251 | B2 | 4/2004 | Bebbington et al. |
| 2003/0162777 | A1 | 8/2003 | Leonardi et al. |
| 2003/0212084 | A1 | 11/2003 | Hatton et al. |
| 2004/0152704 | A1 | 8/2004 | Altenbach et al. |

FOREIGN PATENT DOCUMENTS

| | | |
|---|---|---|
| WO | WO 9943682 | 9/1999 |
| WO | WO 0222601 | 3/2002 |

OTHER PUBLICATIONS

Caulfield & Nigel, International Union of Pharmacology. XVII. Classification of Muscarinic Acetylcholine Receptors, Pharmacological Reviews, 50(2):279-290 (1998), p. 284.*
King, Med Chem.: Principle and Practice (1994), p. 206-208.*
International Search Report, Dated Apr. 26, 2005, International Application No. PCT/US2004/040839.
Abbiati, Giorgio, et al, "An efficient synthesis of 2,4-substituted [1,8] naphthyridines from 3-(2-Amino-5-methylpyridin-3-yl)-1-arylprop-2-yn-1-ones", *Synthesis*, No. 13, pp. 1912-1916 (2002).
Carboni, S., et al., "Preparation and pharmacological study on some 1,2,3-triazolyl-1,8-naphthyridine derivatives," *Farmaco, Edizione Scientifica*, 33(5), pp. 315-323 (1978).
Caulfield, Malcolm P. et al., "Muscarinic Receptors-Characterization, Coupling, and Function," *Pharmacol. Ther.* vol. 58, pp. 319-379 (1993).
Caulfield, Malcolm P. et al. "International Union of Pharmacology, XVII. Classification of Muscarinic Acetylcholine Receptors," *Pharmacological Reviews*, vol. 50, No. 2, pp. 279-290 (1998).
Delapp, Neil et al., "Therapeutic Opportunities for Muscarinic Receptors in the Central Nervous System," *Journal of Medicinal Chemistry*, vol. 43 No. 23, pp. 4333-4353 (2000).
Ferrarini, Pier Luigi, et al., "Synthesis and antiplatelet activity of some 1,8-naphthyridine derivatives," *European Journal of Medicinal Chemistry*, Editions Scientifique Elsevier, Paris, Fr., vol. 29, pp. 735-741(1994).
Ferrarini, Pier Luigi, et al., "A novel class of highly potent and selective A1 adenosine antagonists—Structure-affinity profile of a series of 1,8-naphthyridine derivatives," *Journal of Medicinal Chemistry*, vol. 43, No. 15, pp. 2814-2823 (2000).
Ferrarini, Pier Luigi, et al., "Study on Affinity Profile toward Native Human and Bovine Adenosine Receptors of a Series of 1,8-Naphthyridine Derivatives," *Journal of Medicinal Chemistry*, vol. 47 No. 12, pp. 3019-3031 (2004).
Ferrarini, Pier Luigi, et al., "Synthesis of bis(2-chloroethyl)amino-1,8-naphthyridines for evaluation as anticancer agents," *Journal of Heterocyclic Chemistry*, vol. 21 No. 2 pp. 417-419 (1984).
Hulme, E.C. et al., "Muscarinic Receptor Subtypes," *Annual Reviews Pharmacol. Toxicol.*, vol. 30, pp. 633-673 (1990).
Macchia, Marco, et al., "4-'6-(Dansylamino)-hexylamino!-7-methyl-2-phenyl-1,8-naphthyridine as a new potential fluorescent probe for studying A1-adenosine receptor" *IL Farmaco*, vol. 57, No. 10, pp. 783-786 (2002).
Rivalle, Christian & Bisagni, Emile, "Ethyl (4-N-Acylaminopyridin-3-yl) glyoxylate and 5-Azaisatin as New Synthons for a Route to Various New Polyheterocycles" *Journal of Heterocyclic Chem.*, vol. 34, pp. 441-444 (1997).
Turner, James A., "Regiospecific Electrophilic Substitution of Aminopyridines: Ortho Lithiation of 2-,3-, and 4-(Pivaloylamino) pyridines" *Journal Org. Chem.*, vol. 48, pp. 3401-3408, (1983).
Zlokarnik, Gregor, et al., "Quantitation of transcription and clonal selection of single living cells with β-lactamase as reporter" *Science*, vol. 279, pp. 84-88 (1998).

* cited by examiner

*Primary Examiner*—Taofiq A Solola
(74) *Attorney, Agent, or Firm*—Miller Canfield; Andrew N. Weber

(57) ABSTRACT

The modulator compounds described herein modulate muscarinic receptors and are useful for treating muscarinic receptor mediated diseases.

8 Claims, No Drawings

MODULATORS OF MUSCARINIC RECEPTORS

This application claims priority under 35 U.S.C. §119 (e) to U.S. Provisional Application Ser. No. 60/528,049 filed on Dec. 9, 2003.

TECHNICAL FIELD OF THE INVENTION

The present invention relates to compounds useful as therapeutic agents. The invention also provides pharmaceutically acceptable compositions comprising the compounds of the invention and methods of using the compositions in the treatment of various disorders.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptoin thrs. See, e.g., DeLapp, N. et al., "Therapeutic Opportunities for Muscarinic Receptors e Central Nervous System," *J. Med. Chem.*, 43(23), pp. 4333-4353 (2000); Hulme, E. C. et al., "Muscarinic Receptor Subtypes," *Ann. Rev. Pharmacol. Toxicol.*, 30, pp. 633-673 (1990); Caulfield, M. P. et al., "Muscarinic Receptors-Characterization, Coupling, and Function," *Pharmacol. Ther.*, 58, pp. 319-379 (1993); Caulfield, M. P. et al., International Union of Pharmacology. XVII. Classification of Muscarinic Acetylcholine Receptors," *Pharmacol. Rev.*, 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors), and Pain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain on the other had may last for much longer periods of time and it's intensity is more graded. Inflammation may occur for many reasons including tissue damage, autoimmune response, and pathogen invasion. Inflammatory pain is mediated by an "inflammatory soup" that consists of substance P, histamines, acid, prostaglandin, bradykinin, CGRP, cytokines, ATP, and neurotransmitter release. The third class of pain is neuropathic and involves nerve damage that results in reorganization of neuronal proteins and circuits yielding a pathologic "sensitized" state that can produce chronic pain lasting for years. This type of pain provides no adaptive benefit and is particularly difficult to treat with existing therapies.

Pain, particularly neuropathic and intractable pain is a large unmet medical need. Millions of individuals suffer from severe pain that is not well controlled by current therapeutics. The current drugs used to treat pain include NSAIDS, COX2 inhibitors, opioids, tricyclic antidepressants, and anticonvulsants. Neuropathic pain has been particularly difficult to treat as it does not respond well to opiods until high doses are reached. Gabapentin is currently the favored therapeutic for the treatment of neuropathic pain although it works in only 60% of patients where it shows modest efficacy. The drug is however very safe and side effects are generally tolerable although sedation is an issue at higher doses.

Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides a method of modulating activity of a muscarinic receptor, comprising the step of contacting said receptor with a compound of formula I:

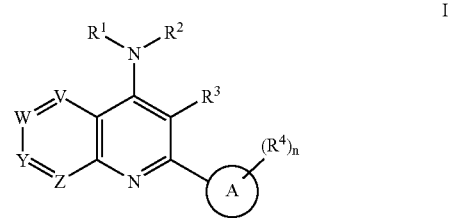

wherein:

Ring A is aryl or heteroaryl;

One of V, W, Y or Z is nitrogen and the other of V, W, Y and Z are —C($R^5$)—;

Each $R^1$ is independently selected from H, aliphatic, cycloaliphatic, heteroaliphatic and heterocycle, wherein each of the aliphatic, cycloaliphatic, heteroaliphatic and heterocycle is optionally substituted with 1-3 Ra;

Each $R^2$ is independently selected from H, aryl, heteroaryl, aliphatic, cycloaliphatic, heteroaliphatic, heterocycle, —C(O)Rc, and —S(O)$_2$Rc, wherein each aliphatic, cycloaliphatic, heteroaliphatic and heterocycle is optionally substituted with 1-3 Ra, and wherein each aryl and heteroaryl is optionally substituted with 1-3 Rb, or $R^1$ and $R^2$ together with the nitrogen to which they are attached may form a heterocyclic ring or a heteroaryl ring each optionally substituted with 1-3 Ra;

Each $R^3$ is independently H, halo, haloaliphatic, aliphatic, —ORd, or —S(O)$_i$Rd;

Each $R^4$ is independently selected from H, halogen, —CN, —OH, —NO$_2$, —ORd, —C(O)Rd, —C(O)ORd, —C(O)N(Rd)$_2$, —N(Rd)$_2$, —N(Rd)C(O)Rd, —N(Rd)C(O)ORd, —OC(O)ORd, —OC(O)NRd, —N(Rd)S(O)$_2$Rd, aliphatic optionally substituted with 1-3 Ra, and any two adjacent $R^4$ on Ring A together with the atoms to which they are attached may be taken together to form a heterocyclic or carbocyclic ring;

Each $R^5$ is independently selected from H, halogen, —CN, —OH, —NO$_2$, —ORd, —C(O)Rd, —C(O)ORd, —C(O)N(Rd)$_2$, —N(Rd)$_2$, —N(Rd)C(O)Rd, —N(Rd)C(O)ORd, —OC(O)ORd, —OC(O)NRd, —N(Rd)S(O)$_2$Rd, aliphatic optionally substituted with 1-3 of Ra, and any two adjacent $R^5$ together with the atoms to which they are attached may be taken together to form a heterocyclic or carbocyclic ring;

Each Ra is independently selected from aryl, heteroaryl, halogen, —CN, —OH, —ORd, —C(O)Rd, —C(O)ORd, —C(O)N(Rd)$_2$, —N(Rd)$_2$, —NRdC(O)Rd, —N(Rd)C(O)ORd, —N(Rd)C(O)N(Rd)$_2$, —OC(O)ORd, —OC(O)N(Rd)$_2$, =N—OH, =NORd, =N=N(Rd)$_2$, =O, =S, —S(O)$_2$N(Rd)$_2$, —N(Rd)S(O)$_2$Rd, —N(Rd)S(O)$_2$N(Rd)$_2$ and —S(O)$_i$Rd;

Each Rb is independently selected from halo, aryl, —OH, —ORd, —S(O)$_i$Rd, —N(Rd)$_2$, —NRdC(O)Rd, —NRdC(O)ORd, —C(O)Rd, —C(O)ORd, —C(O)N(Rd)$_2$, —S(O)$_i$N(Rd)$_2$, —CN, and —NO$_2$;

Each Rc is independently selected from H, aliphatic, cycloaliphatic, heteroaliphatic, heterocycle, aryl, heteroaryl, —ORd, and —N(Rd)$_2$, wherein the aliphatic, cycloaliphatic, heteroaliphatic, heterocycle, aryl, and heteroaryl are optionally substituted with 1-3 of Ra;

Each Rd is independently selected from H, aliphatic, heteroaliphatic, heterocycle, cycloaliphatic, aryl, and heteroaryl, wherein each of aliphatic, heteroaliphatic, heterocycle, cycloaliphatic, aryl, heteroaryl may be optionally substituted with 1-3 of halo, aryl, —OH, —Oaliphatic, —Oaryl, —Oacyl, —NH$_2$, —N(aliphatic)$_2$, —N(aryl)$_2$, —S(O)$_i$aliphatic, or —S(O)$_i$aryl;

n is 0 to 3; and i is 0 to 2.

The present invention also provides compounds of formula (I), compositions comprising compounds of formula (I), and methods of treating muscarinic receptor mediated diseases using compounds of formula (I).

Advantageously, the compounds of the invention unexpectedly modulate muscarinic receptors.

DETAILED DESCRIPTION OF THE INVENTION

I. Definitions

As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders,pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradhycardia, gastric acid secretion, asthma, GI disturbances and wound healing.

The phrase "optionally substituted" is used interchangeably with the phrase "substituted or unsubstituted." As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. As one of ordinary skill in the art will recognize, combinations of substituents envisioned by this invention are those combinations that result in the formation of stable or chemically feasible compounds.

The phrase "stable or chemically feasible", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloaliphatic"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted aliphatic, alkenyl, alkynyl groups and hybrids thereof such as (cycloaliphatic)aliphatic, (cycloalkenyl)aliphatic or (cycloaliphatic)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quatemized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioaliphatic", as used herein, refers to an aliphatic group, as previously defined, attached to the principal carbon chain through an oxygen ("alkoxy") or sulfur ("thioaliphatic") atom.

The terms "haloaliphatic", "haloalkenyl" and "haloalkoxy" means aliphatic, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyaliphatic", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "amino protecting group" refers to a suitable chemical group that may be attached to a nitrogen atom. The term "protected" refers to when the designated functional group is attached to a suitable chemical group (protecting group). Examples of suitable amino protecting groups and protecting groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

II. Description of Compounds:

In general, the compounds useful for modulating muscarinic activity of muscarinic receptors have the formula I:

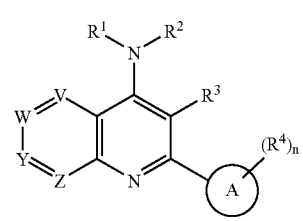

Wherein Ring A, $R^1$, $R^2$, $R^3$, $R^4$, V, W, Y, Z, and n are defined above.

In some aspects, Ring A in formula I is an aryl optionally substituted with 1-3 of $R^4$. Embodiments of this aspect include one or more of the following features. Ring A is phenyl. Ring A is substituted with 1 or 2 of $R^4$. $R^4$ is aliphatic. $R^4$ is $CH_3$. $R^4$ is halogen. $R^4$ is —ORd. $R^4$ is —Oaliphatic. $R^4$ is —$OCH_3$. $R^4$ is haloaliphatic. Two $R^4$ substituents on Ring A together form —O—$CH_2$—O—. Two $R^4$ substituents on Ring A together form —O—$CH_2$—$CH_2$—O—. Z is N. Y is N. W is N. V is N. n is 0. n is 1. n is 2.

In other aspects, A in formula I is an heteroaryl optionally substituted with 1-3 of $R^4$. Embodiments of this aspect include one or more of the following features. Ring A is pyridinyl. Ring A is substituted with 1 or 2 of $R^4$. $R^4$ is aliphatic. $R^4$ is $CH_3$. $R^4$ is halogen. $R^4$ is —ORd. $R^4$ is —Oaliphatic. $R^4$ is —$OCH_3$. $R^4$ is haloaliphatic. Two $R^4$ substituents on Ring A together form —O—$CH_2$—O—. Two $R^4$ substituents on Ring A together form —O—$CH_2$—$CH_2$—O—. Z is N. Y is N. W is N. V is N. n is 0. n is 1. n is 2.

In other embodiments, the compounds of formula I include one or more of the following features.

$R^3$ is H, halo, aliphatic, or —ORd. $R^3$ is H.

$R^1$ is H, aliphatic, or heteroaliphatic, wherein each of the aliphatic and heteroaliphatic is optionally substituted with 1-3 Ra. Each $R^1$ is independently selected from cycloaliphatic and heterocycle each optionally substituted with 1-3 Ra. $R^1$ is H. $R^1$ is aliphatic optionally substituted with 1-3 Ra.

$R^2$ is H, aliphatic, heteroaliphatic, —C(O)Rc, or —$S(O)_2$Rc, wherein each aliphatic and heteroaliphatic is optionally substituted with 1-3 Ra. $R^2$ is H. $R^2$ is —C(O)Rc. $R^2$ is aliphatic optionally substituted with 1-3 Ra. Each $R^2$ is independently selected from aryl and heteroaryl, each optionally substituted with 1-3 Ra, and wherein each aryl and heteroaryl is optionally substituted with 1-3 Rb. Each R2 is independently selected from cycloaliphatic and heterocycle each optionally substituted with 1-3 Ra.

$R^1$ and $R^2$ together with the nitrogen to which they are attached may form a heterocyclic ring optionally substituted with 1-3 Ra.

Each $R^5$ is independently selected from H, halogen, —ORd, —C(O)Rd, —C(O)ORd, —C(O)N$(Rd)_2$, and aliphatic optionally substituted with 1-3 of Ra. Each $R^5$ is independently selected from H, —N$(Rd)_2$, —N(Rd)C(O)Rd, —N(Rd)C(O)ORd, —OC(O)ORd, —OC(O)NRd, and —N(Rd)S$(O)_2$Rd.

Each Ra is independently selected from halogen, —CN, —ORd, —C(O)Rd, —C(O)ORd, —C(O)N$(Rd)_2$, —N$(Rd)_2$, —NRdC(O)Rd, —N(Rd)C(O)ORd, —N(Rd)C(O)N$(Rd)_2$, —OC(O)ORd, —OC(O)N$(Rd)_2$, =O, —S$(O)_2$N$(Rd)_2$, —N(Rd)S$(O)_2$Rd, —N(Rd)S$(O)_2$N$(Rd)_2$ and —S$(O)_i$Rd. Each Ra is independently selected from halogen, —ORd, —C(O)Rd, —C(O)ORd, —C(O)N$(Rd)_2$, —N$(Rd)_2$, —OC(O)ORd, —OC(O)N$(Rd)_2$, and =O. Ra is independently selected from halogen, —CN, —ORd, —C(O)Rd, —C(O)ORd, and =O.

Each Rb is independently selected from halo, aryl, —ORd, —S$(O)_i$Rd, —N$(Rd)_2$, —NRdC(O)Rd, —NRdC(O)ORd, —C(O)Rd, —C(O)ORd, —C(O)N$(Rd)_2$, —S$(O)_i$N$(Rd)_2$, —CN, and —$NO_2$. Each Rb is independently selected from halo, aryl, —ORd, —C(O)Rd, —C(O)ORd, —C(O)N$(Rd)_2$, and —CN. Each Rb is independently selected from halo, aryl, —S$(O)_i$Rd, —N$(Rd)_2$, —NRdC(O)Rd, —NRdC(O)ORd, —S$(O)_i$N$(Rd)_2$, and —$NO_2$. Each Rb is independently selected from halo, —ORd, —S$(O)_i$Rd, and —S$(O)_i$N$(Rd)_2$. Each Rb is independently selected from halo and —ORd, —C(O)Rd, and —C(O)ORd.

Each Rc is independently selected from H, aliphatic, heteroaliphatic, —ORd, and —N$(Rd)_2$, wherein the aliphatic and heteroaliphatic are optionally substituted with 1-3 of Ra. Each Rc is independently selected from H, —ORd, and —N$(Rd)_2$. Each Rc is independently selected from aliphatic and heteroaliphatic each of which are optionally substituted with 1-3 of Ra. Each Rc is independently aliphatic optionally substituted with 1-3 of Ra.

Each Rd is independently selected from H, aliphatic, heteroaliphatic, wherein each of the aliphatic and heteroaliphatic are optionally substituted with 1-3 of halo, —OH, —Oaliphatic, —Oaryl, —Oacyl, —$NH_2$, —N(aliphatic)$_2$, —N(aryl)$_2$, —S$(O)_i$aliphatic, or —S$(O)_i$aryl. Each Rd is independently selected from H, heterocycle, and cycloaliphatic, wherein each of the heterocycle and cycloaliphaticare optionally substituted with 1-3 of halo, aryl, —OH, —Oaliphatic, —Oaryl, —Oacyl, —$NH_2$, —N(aliphatic)$_2$, —N(aryl)$_2$, —S$(O)_i$aliphatic, or —S$(O)_i$aryl. Each Rd is independently selected from H, aryl, and heteroaryl, wherein each of the aryl and heteroaryl are optionally substituted with 1-3 of halo, aryl, —OH, —Oaliphatic, —Oaryl, —Oacyl, —$NH_2$, —N(aliphatic)$_2$, —N(aryl)$_2$, —S$(O)_i$aliphatic, or —S$(O)_i$aryl. Each Rd is independently selected from H and aliphatic optionally substituted with 1-3 of halo, aryl, —OH, —Oaliphatic, —Oaryl, —Oacyl, —$NH_2$, —N(aliphatic)$_2$, —N(aryl)$_2$, —S$(O)_i$aliphatic, or —S$(O)_i$aryl.

In other embodiments, the compounds have the structure of formula I provided (i) when A is 2-trifluoromethylphenyl, one of Z or Y is N and the remaining of W, V, Y, or Z is —C(H)—, $R^3$ is H, and $R^1$ is H, then $R^2$ is not indazolyl, pyrazolyl, or triazolyl each optionally substituted with aliphatic, phenyl, and —C(O)O-aliphatic;

(ii) when A is phenyl, V is N and W, Y and Z are —C(H)—, $R^3$ is H, that $R^1$ and $R^2$ together with the nitrogen to which they are bound do not form piperidine optionally substituted with —C(O)O-aliphatic, —C(O)N(H)-aliphatic, or —C(O)OH;

(iii) when A is phenyl, V is N and W, Y and Z are —C(H)—, $R^3$ is H, and $R^1$ is H, that $R^2$ is not —$CH_2$-piperidine;

(iv) when A is phenyl optionally substituted with one $R^4$, Z is N, V and W are —C(H)—, and $R^3$ is H, that Y is other than —C(aliphatic)-;

(v) when A is phenyl optionally substituted with one $R^4$, Z is N, Y and V are —C(H)—, and $R^3$ is H, that W is other than —C(aliphatic)-;

(vi) when A is pyridinyl, Z is N, $R^1$ is H, $R^3$ is H, and V, W, and Y are —C(H)—, that $R^2$ is not —$(CH_2)_2$—N(aliphatic)$_2$.

In still other aspects, the invention features compounds of formula I that include combinations of the different aspects and embodiments described above. For instance, embodiments of compounds of formula I where Ring A is aryl may include one or more of the embodiments described above for $R^1$, $R^2$, $R^3$, $R^5$, Ra, Rb, Rc, and Rd.

Exemplary compound of formula I are show in Table 1.
TABLE 1
Exemplary Compounds of Formula I.
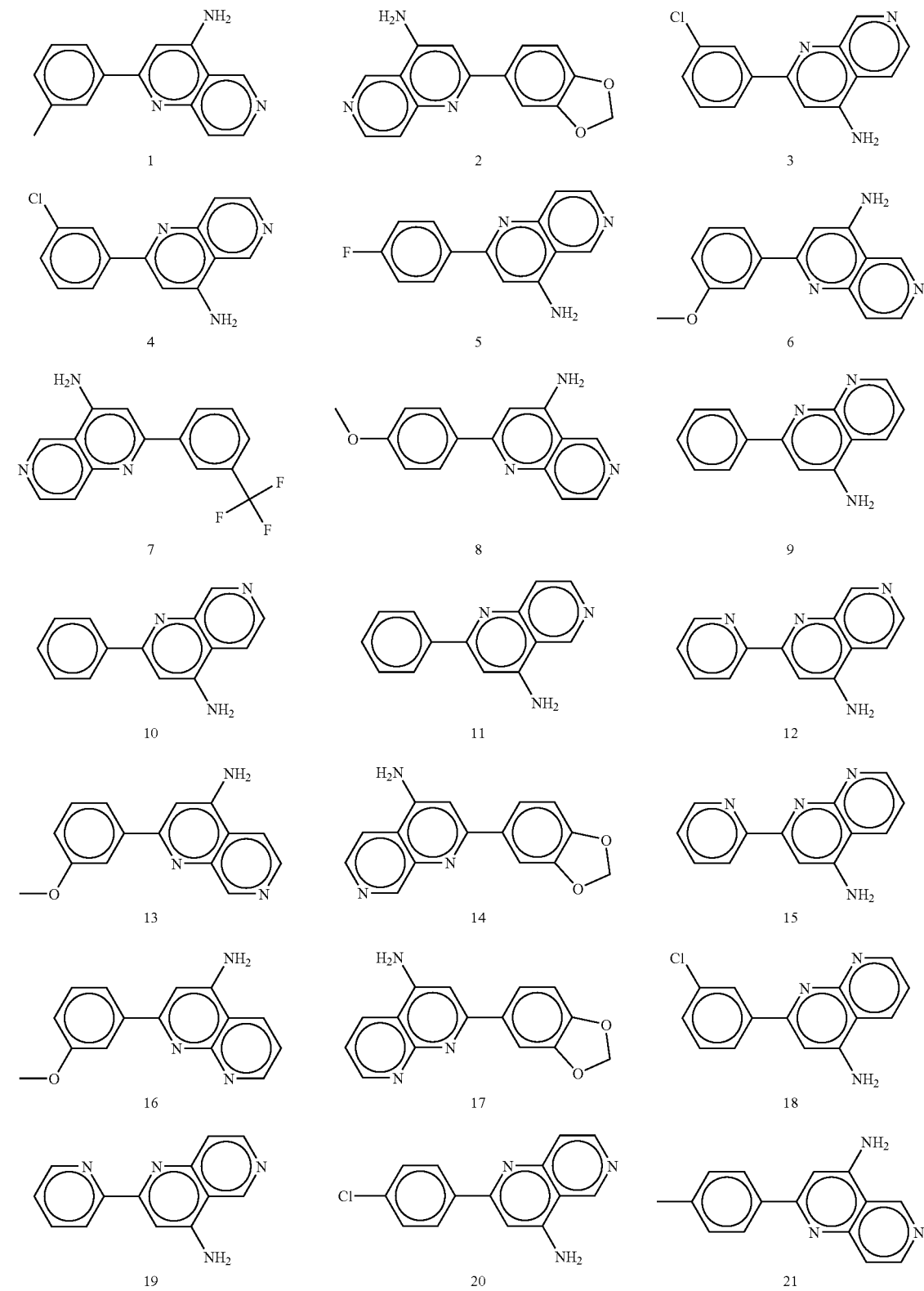

TABLE 1-continued

Exemplary Compounds of Formula I.

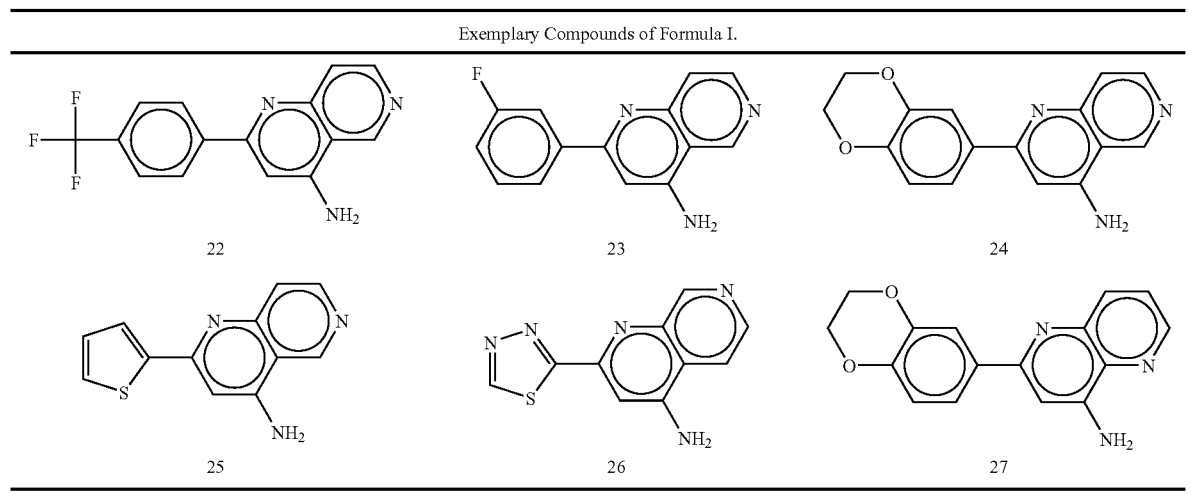

III. General Synthetic Methodology

The compounds of this invention may be prepared in general by methods known to those skilled in the art for analogous compounds, as illustrated by the general schemes below, and the preparative examples that follow. Starting materials are commercially available from typical chemical reagent supply companies, such as, Aldrich Chemicals Co., Sigma Chemical Company, and the like. Compounds that are not commercially available can be prepared by those of ordinary skill in art following procedures set forth in references such as, "Fieser and Fieser's Reagents for Organic Synthesis", Volumes 1-15, John Wiley and Sons, 1991; "Rodd's Chemistry of Carbon Compounds", Volumes 1-5 and Supplementals, Elsevier Science Publishers, 1989; and "Organic Reactions", Volumes 1-40, John Wiley and Sons, 1991.

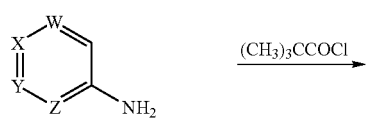

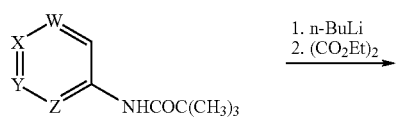

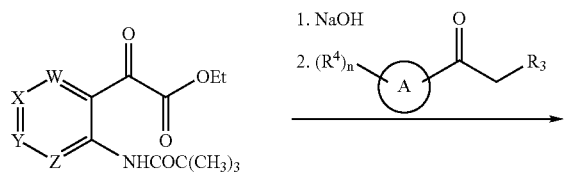

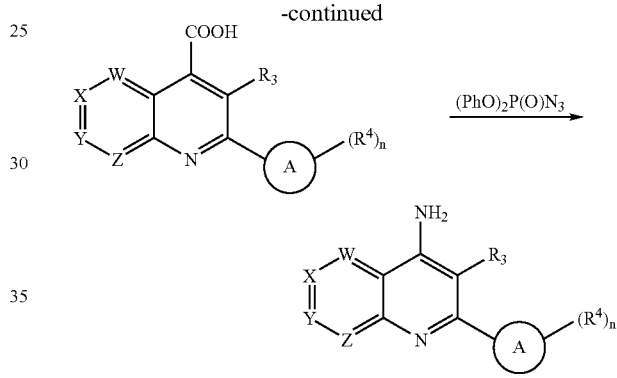

Directed metalation of optionally substituted pyridines followed by quenching by a suitable reagent, such as ethyl oxalate, afforded the corresponding α-ketoesters. Removal of the protecting group followed by condensation with a suitable ketone, for example an acetophenone, and acid-catalyzed cyclization afforded various [1,n]naphthyridine carboxylates in moderate to good yields. These compounds were subjected to the Curtius rearrangement to afford the corresponding amino naphthyridines. The preparation of certain compounds of the present invention are taught in Examples 1 to 4.

Other methods for producing the compounds are known in the art. For example, 1,5-naphthyridines may be prepared according to methods described in U.S. application Nos. 20030212084 and 20040152704, European Application No. 487242, and PCT Publication Nos. WO9943682 and WO0047580. Each of these references is incorporated herein.

In still further aspects, the compound of the formula II are useful in preparing the compound of formula I

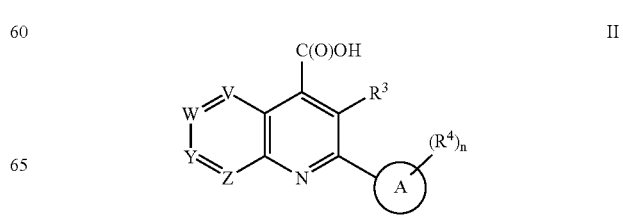

wherein each of Ring A, V, W, Y, Z, $R^3$, $R^4$ and n are defined above.

IV. Uses, Formulations, Compositions, and Administration

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, flimarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., calcium or magnesium), ammonium and $N^+(C_{1-4}$ alkyl$)_4$ salts or salts of lysine and arginine. This invention also envisions the quaternization of any basic nitrogen-containing groups of the compounds disclosed herein. Water or oil-soluble or dispersible products may be obtained by such quaternization. Other salts can be found in "Practical Process, Research, & Development," Anderson, Neal G., Academic Press, 2000, the contents of which are incorporated herein by reference.

The compositions of the present invention may be administered orally, parenterally, by inhalation spray, topically, rectally, intermuscularly, subcutaneously, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formula I are selective modulators of $M_1$, $M_2$ and $M_4$. More preferably, the compounds of formula (I, IA, II, and III) are selective modulators of $M_1$ and $M_4$. Or, the compounds of formula (I, IA, II, and III) are selective modulators of $M_2$ and $M_4$. Yet more preferably, the compounds of formula (I, IA, II, and III) are selective modulators of one of $M_1$, $M_2$, and $M_4$. The compounds of formula (I, IA, II, and III) are selective modulators of $M_4$. The compounds of formula (I, IA, II, and III) are selective modulators of $M_1$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e, an agonist) or inhibits the activity of a muscarinic receptor.

According to another embodiment, the compounds of formula (I, IA, II, and III) are selective activators of all of $M_1$, $M_2$, and $M_4$. In other embodiments, the compounds of formula (I, IA, II, and III) are selective activators of one of $M_1$, $M_2$, and $M_4$ and selective inhibitors of the other two of $M_1$, $M_2$, and $M_4$. In another embodiment, the compounds of formula (I, IA, II, and III) are selective activators of up to two of $M_1$, $M_2$, and $M_4$ and selective inhibitors of the other of $M_1$, $M_2$, and $M_4$. In still another embodiment, the compounds of formula (I, IA, II, and III) are selective inhibitors of all of $M_1$, $M_2$, and $M_4$.

According to another embodiment, the compounds of compounds of formula (I, IA, II, and III) are selective inhibitors of one or more of $M_1$, $M_2$, or $M_4$. In one embodiment, preferably, the compounds of formula (I, IA, II, and III) are selective inhibitors of $M_4$. In another embodiment, the compounds of formula I are selective inhibitors of $M_1$. In yet another embodiment, the compounds of formula I are selective inhibitors of $M_1$ and $M_4$. In still another embodiment, the compounds of formula I are selective inhibitors of $M_1$ and $M_2$ or $M_4$ and $M_2$.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, comprising the step of administering to said mammal a composition comprising a compound of formula I, or a preferred embodiment thereof as set forth above.

According to a preferred embodiment, the present invention provides a method of treating a disease mediated by one or more of $M_1$, $M_2$, or $M_4$, comprising the step of administering to said mammal a composition comprising a compound of formula (I, IA, II, and III), or a preferred embodiment thereof as set forth above. Or in another embodiment the disease is mediated by $M_2$. Or, said disease is mediated by $M_1$. Yet more preferably, said disease is mediated by $M_4$. In still further embodiments, the disease is mediate by all of $M_1$, $M_2$, and $M_4$. In another embodiment, the disease is mediate by two of $M_1$, $M_2$, and $M_4$.

According to a preferred embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis associated with CNS disorders including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, and wound healing, wherein said method comprises the step of contacting said patient with a compound according to the present invention.

In one embodiment, the present invention provides a method for the treatment or lessening the severity of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, post-surgical pain, back pain, or cancer pain is provided comprising administering an effective amount of a compound or a pharmaceutically acceptable composition to a subject in need thereof.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradycardia, gastric acid secretion, asthma, GI disturbances or wound healing.

According to a preferred embodiment, the present invention is useful for treating or reducing the severity of psychosis, Alzheimer's disease, pain, or Parkinson's disease.

In order that the invention described herein may be more fully understood, the following examples are set forth. It should be understood that these examples are for illustrative purposes only and are not to be construed as limiting this invention in any manner.

All references cited above are incorporated herein by reference.

Other embodiments of the compounds of formula I are shown below. The following examples are illustrative of the compounds of formula I and are not meant to be limiting.

EXAMPLES

Example 1

Preparation of 2,2-Dimethyl-N-pyridinyl-propionamides

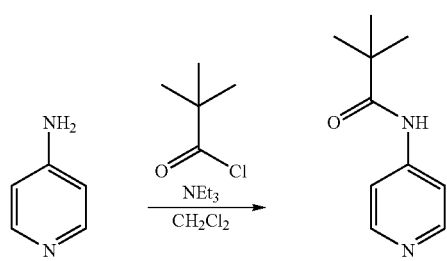

1A: 2,2-Dimethyl-N-pyridin-4-yl-propionamide

Following procedures generally taught in J. A. Turner, *J. Org. Chem.* 1983, 48, 3401-3408, a solution of pivaloyl chloride (13.5 mL, 110 mmol) in $CH_2Cl_2$ (20 mL) was slowly added to an ice-cold solution of 4-aminopyridine (9.41 g, 100 mmol) and triethylamine (17.4 mL, 125 mmol) in $CH_2Cl_2$ (150 mL). After addition was complete, the resulting mixture was warmed to room temperature and stirred for 2 h. The solution was poured into water, the $CH_2Cl_2$ layer was washed with dilute $NaHCO_3$, dried over Na2SO4, and evaporated to leave a light brown solid. Recrystallization from EtOAc/hexanes afforded the product as a white crystal, which was collected by vacuum filtration (13.03 g, 73%). $^1$H NMR (400 MHz, $CDCl_3$) δ 8.50 (d, J=4.8 Hz, 2 H), 7.50 (d, J=4.8 Hz, 2 H), 7.44 (br s, 1 H), 1.33 (s, 9 H). MS (LR-APCI) calcd. for $C_{10}H_{15}N_2O$ (M+H) 179.1; found 179.1.

1B: 2,2-Dimethyl-N-pyridin-2-yl-propionamide

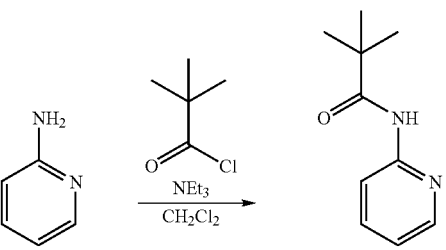

Following the procedure taught in Example 1A, the title compound was prepared having the following characteristics (white powder, 14.4 g. 81%). $^1$H NMR (400 MHz, $CDCl_3$) δ 8.28-8.24 (m, 2 H), 7.99 (br s, 1 H), 7.72-7.68 (m, 1 H), 7.05-7.02 (m, 1 H), 1.71 (s, 9 H). MS (LR-APCI) calcd. for $C_{10}H_{15}N_2O$ (M+H) 179.1; found 179.1.

1C: 2,2-Dimethyl-N-pyridin-3-yl-propionamide

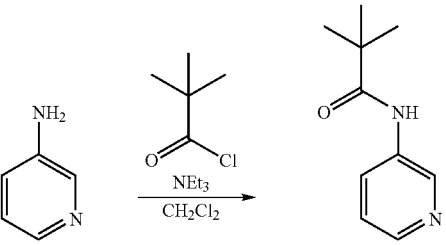

Following the procedure taught in Example IA, the title compound was prepared having the following characteristics (white solid, 13.90 g, 78%). $^1$H NMR (400 MHz, $CDCl_3$) δ 8.56-8.54 (m, 1 H), 8.36-8.34 (m, 1 H), 8.22-8.18 (m, 1 H), 7.39 (br s, 1 H), 7.30-7.26 (m, 1 H), 1.34 (s, 9 H). MS (LR-APCI) calcd. for $C_{10}H_{15}N_2O$ (M+H) 179.1; found 479.2.

Example 2

Preparation of (2,2-Dimethyl-propionylamino)-pyridinyl-oxo-acetic acid ethyl esters

2A: [4-(2,2-Dimethyl-propionylamino)-pyridin-3-yl]-oxo-acetic acid ethyl ester

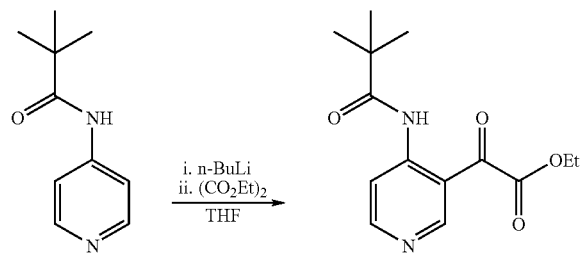

Following procedures generally taught in J. A. Turner, *J. Org. Chem.* 1983, 48, 3401-8; and C. Rivalle & E. Bisagni, *J. Heterocyclic Chem.*, 1997, 34, 441-4, a 3-necked, 500 mL round bottom flask with thermometer and addition funnel were flame-dried under $N_2$. 2,2-Dimethyl-N-pyridin-3-yl-propionamide (4.46 g, 25.0 mmol) was added, followed by THF (50 mL). The solution was cooled to −78° C. (to control the pending exotherm), and n-BuLi (39 mL of a 1.6 M solution in hexanes, 2.5 equiv) was added dropwise via addition funnel with vigorous stirring of the slurry, keeping internal temp below −50° C. during addition. Once the n-BuLi addition was complete (the solution was yellow and homogeneous), the mixture was warmed to 0° C. for 3 h (a white precipitate emerges). The solution was cooled back down to −78° C. and diethyl oxalate (8.84 mL, 2.6 equiv) in THF (13 mL) was added dropwise via syringe (mild exotherm observed). Once the addition was complete, the reaction was stirred 15 min at −78° C., then warmed to room temperature over 15 min and stirred an additional 15 min (a dark red-orange solution emerges as the solution was stirred at room temperature). The mixture was poured onto ice and extracted with $Et_2O$, washing the extract once with water. The solution was dried ($MgSO_4$), filtered, and concentrated to a dark orange oil. Purification by biotage (50% EtOAc/hexanes) afforded the product as an orange oil (3.61 g, 52%). $R_f$ (prod)= 0.57 (50% EtOAc/hexanes). $^1$H NMR (400 MHz, DMSO-$d_6$) δ 10.69 (s, 1 H), 8.79 (s, 1 H), 8.66 (d, J=6.4 Hz, 1 H), 8.00 (d, J=5.6 Hz, 1 H), 4.32 (q, J=7.0 Hz, 2 H), 1.28 (t, J=7.0 Hz, 3 H), 1.21 (s, 9 H). MS (LR-APCI) calcd. for $C_{14}H_{19}N_2O_4$ (M+H) 279.1; found 279.1.

2B: [2-(2,2-Dimethyl-propionylamino)-pyridin-3-yl]-oxo-acetic acid ethyl ester

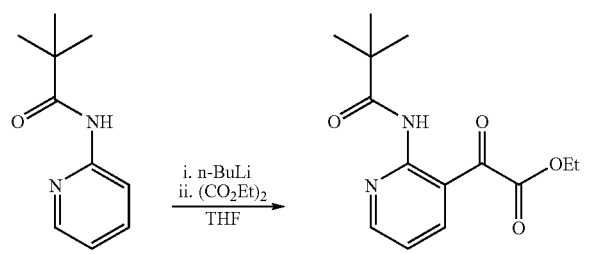

Following the procedure taught in Example 2A, the title compound was prepared having the following characteristics (off-white solid, 1.90 g, 27%). $R_f$ (prod)=0.36 (50% EtOAc/hexanes). $^1$H NMR (400 MHz, DMSO-$d_6$) δ 10.48 (s, 1 H), 8.56-8.53 (m, 1 H), 7.99-7.95 (m, 1 H), 7.35-7.30 (m, 1 H), 4.21-4.14 (m, 2 H), 1.25-1.19 (m, 3 H), 1.14 (s, 9 H). (t, J=7.0 Hz, 3 H), 1.21 (s, 9 H). MS (LR-APCI) calcd. for $C_{14}H_{19}N_2O_4$ (M+H) 279.1; found 279.0.

2C: [3-(2,2-Dimethyl-propionylamino)-pyridin-4-yl]-oxo-acetic acid ethyl ester

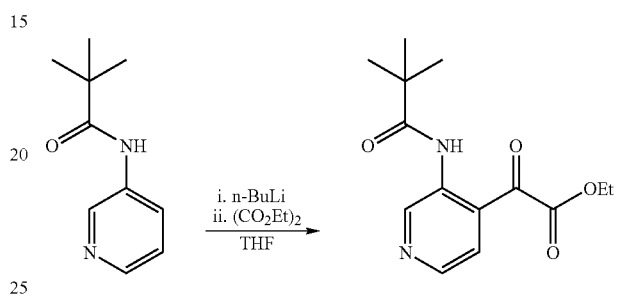

Following the procedure taught in Example 2A, the title compound was prepared having the following characteristics (yellow solid, 1.57 g, 23%). $R_f$ (prod)=0.22 (40% EtOAc/hexanes). $^1$H NMR (400 MHz, CDCl$_3$) δ 10.83 (s, 1 H), 10.15 (s, 1 H), 8.52 (d, J=5.6 Hz, 1 H), 7.57 (d, J=5.6 Hz, 1 H), 4.50 (q, J=7.0 Hz, 2 H), 1.45 (t, J=7.0 Hz, 3 H), 1.37 (s, 9 H). MS (LR-APCI) calcd. for $C_{14}H_{19}N_2O_4$ (M+H) 279.1; found 279.1.

Example 3

Preparation of Naphthyridine-4-carboxylic acids

3A: 2-Phenyl-[1,6]naphthyridine-4-carboxylic acid

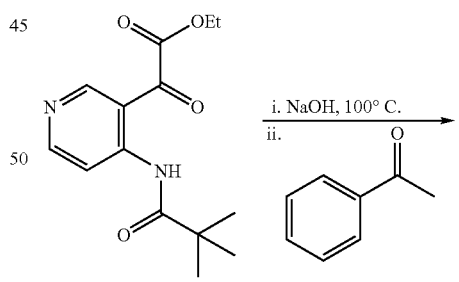

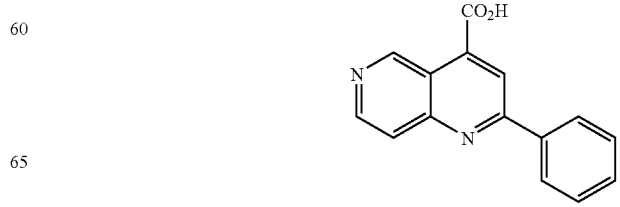

[4-(2,2-Dimethyl-propionylamino)-pyridin-3-yl]-oxo-acetic acid ethyl ester (532 mg, 1.91 mmol) was taken up in ethanol (1.9 mL) and 4N KOH (1.9 mL, 4 equiv) was added. The solution was refluxed for 2-3 h at 100° C., acetophenone (0.446 mL, 2.0 equiv) was added neat, and the reaction was allowed to reflux overnight. Upon cooling to room temperature, the solution was diluted with 1N NaOH and extracted twice with ether. The product was precipitated from the aqueous layer by the addition of glacial AcOH (5-10 mL). The solids were collected by vacuum filtration, rinsed with cold water, and dried under high vacuum (white solid, 371 mg, 78%). $^1$H NMR (400 MHz, DMSO-d$_6$) δ 10.00 (s, 1 H), 8.80 (d, J=5.6 Hz, 1 H), 8.56 (s, 1 H), 8.35-8.31 (m, 2 H), 8.03 (d, J=6.0 Hz, 1 H), 7.61-7.58 (m, 3 H). MS (LR-APCI) calcd. for $C_{15}H_{11}N_2O_2$ (M+H) 251.1; found 251.5.

3B: 2-Phenyl-[1,8]naphthyridine-4-carboxylic acid

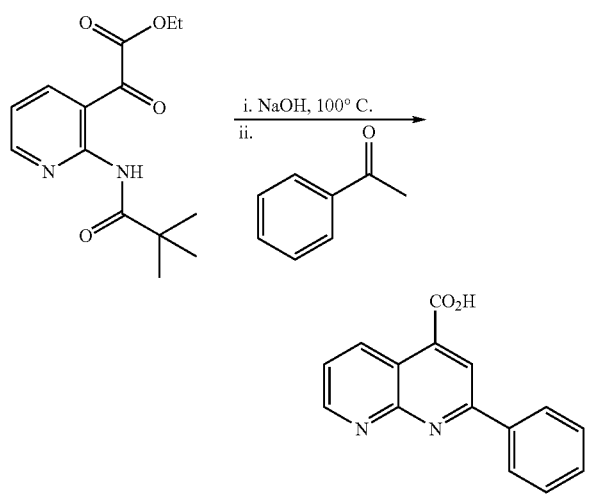

Following the procedure taught in Example 3A, the title compound was prepared having the following characteristics (off-white solid, 380 mg, 84%). $^1$H NMR (400 MHz, DMSO-d$_6$) δ 9.16-9.14 (m, 1 H), 9.12-9.09 (m, 1 H), 8.57 (s, 1 H), 8.35-8.32 (m, 2 H), 7.71 (dd, J=8.6, 3.8 Hz, 1 H), 7.62-7.56 (m, 1 H). MS (LR-APCI) calcd. for $C_{15}H_{11}N_2O_2$ (M+H) 251.1; found 251.5.

3C: 2-Phenyl-[1,7]naphthyridine-4-carboxylic acid

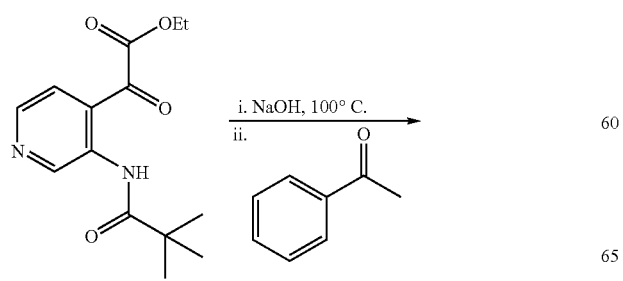

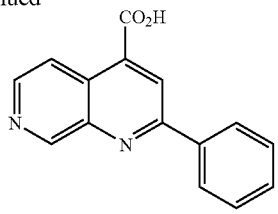

Following the procedure taught in Example 3A, the title compound was prepared having the following characteristics (white solid, 160 mg, 35%). $^1$H NMR (400 MHz, DMSO-d$_6$) δ 9.51 (s, 1 H), 8.72 (s, 1 H), 8.68 (d, J=6.4 Hz, 1 H), 8.56 (d, J=6.4 Hz, 1 H), 8.34-8.30 (m, 2 H), 7.62-7.54 (m, 3 H). MS (LR-APCI) calcd. for $C_{15}H_{11}N_2O_2$ (M+H) 251.1; found 251.5.

3D: 2-Pyridin-2-yl-[1,7]naphthyridine-4-carboxylic acid

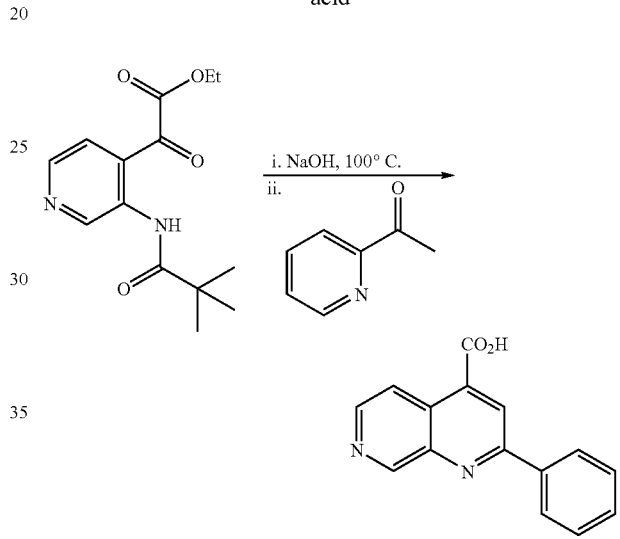

Following the procedure taught in Example 3A, the title compound was prepared having the following characteristics (77 mg, 34%). MS (LR-APCI) calcd. for $C_{14}H_{10}N_3O_2$ (M+H) 252.1; found 252.3.

3E: 2-(3-Methoxy-phenyl)-[1,7]naphthyridine-4-carboxylic acid

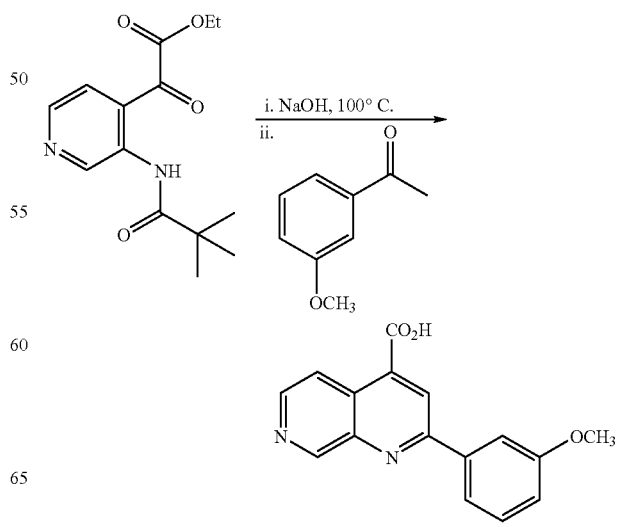

Following the procedure taught in Example 3A, the title compound was prepared having the following characteristics (70 mg, 28%). MS (LR-APCI) calcd. for $C_{16}H_{13}N_2O_3$ (M+H) 281.1; found 281.4.

3F: 2-Benzo[1,3]dioxol-5-yl-[1,7]naphthyridine-4-carboxylic acid

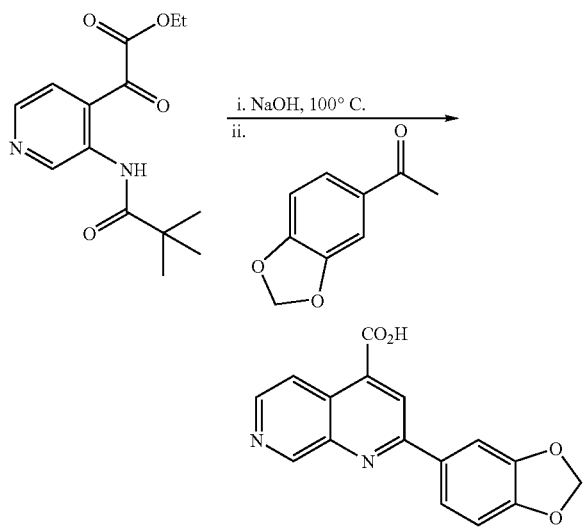

Following the procedure taught in Example 3A, the title compound was prepared having the following characteristics (89 mg, 34%). MS (LR-APCI) calcd. for $C_{16}H_{11}N_2O_4$ (M+H) 295.1; found 295.5.

3G: 2-(3-Chloro-phenyl)-[1,7]naphthyridine-4-carboxylic acid

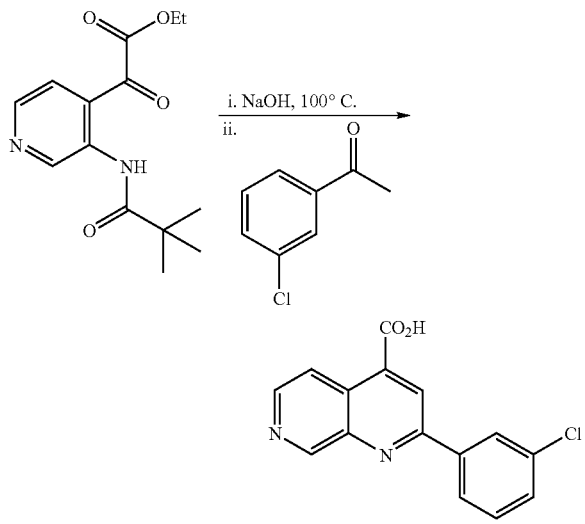

Following the procedure taught in Example 3A, the title compound was prepared having the following characteristics (tan solid, 73 mg, 29%). MS (LR-APCI) calcd. for $C_{15}H_{10}ClN_2O_2$ (M+H) 285.0; found 285.6.

3H: 2-Pyridin-2-yl-[1,8]naphthyridine-4-carboxylic acid

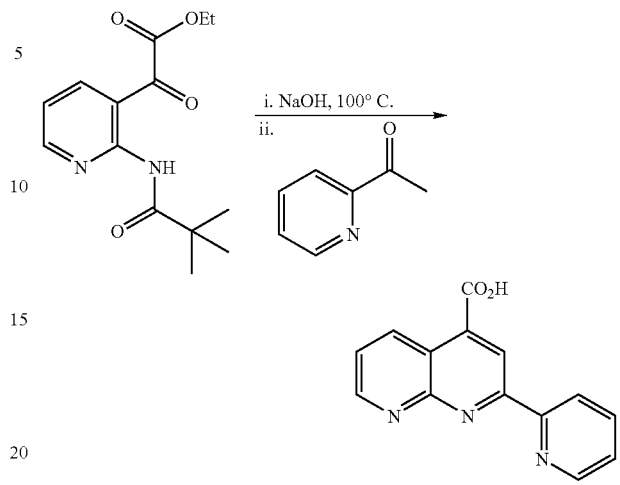

Following the procedure taught in Example 3A, the title compound was prepared having the following characteristics (gray solid, 199 mg, 66%). MS (LR-APCI) calcd. for $C_{14}H_{10}N_3O_2$ (M+H) 252.1; found 252.4.

3I: 2-(3-Methoxy-phenyl)-[1,8]naphthyridine-4-carboxylic acid

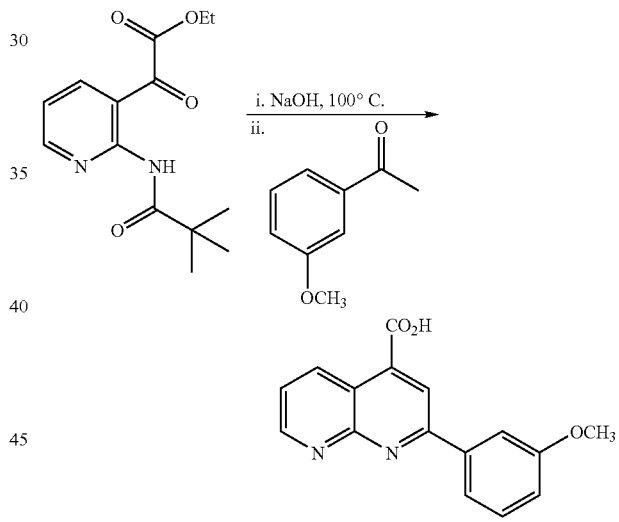

Following the procedure taught in Example 3A, the title compound was prepared having the following characteristics (yellow solid, 252 mg, 75%). MS (LR-APCI) calcd. for $C_{16}H_{13}N_2O_3$ (M+H) 281.1; found 281.4.

3J: 2-Benzo[1,3]dioxol-5-yl-[1,8]naphthyridine-4-carboxylic acid

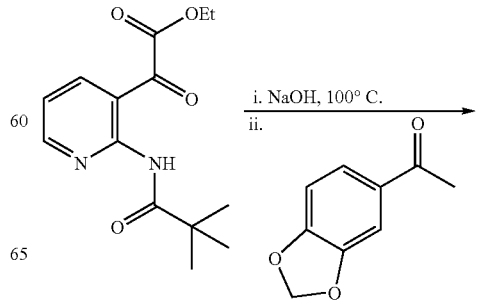

-continued

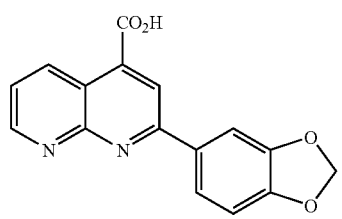

Following the procedure taught in Example 3A, the title compound was prepared having the following characteristics (golden solid, 298 mg, 84%). MS (LR-APCI) calcd. for $C_{16}H_{11}N_2O_4$ (M+H) 295.1; found 295.4.

3K: 2-(3-Chloro-phenyl)-[1,8]naphthyridine-4-carboxylic acid

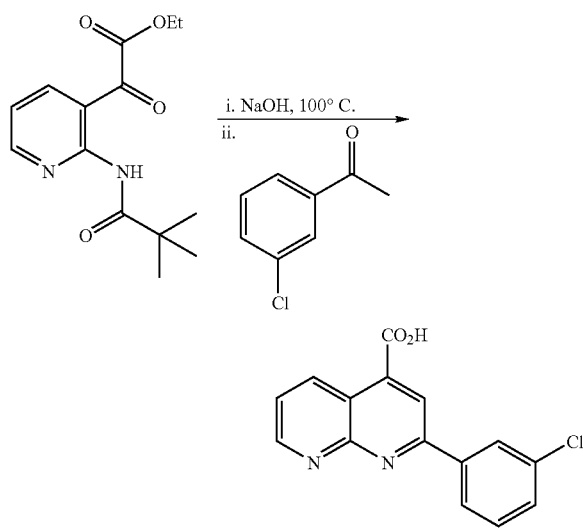

Following the procedure taught in Example 3A, the title compound was prepared having the following characteristics (white solid, 251 mg, 73%). MS (LR-APCI) calcd. for $C_{15}H_{10}ClN_2O_2$ (M+H) 285.0; found 285.4.

3L: 2-Pyridin-2-yl-[1,6]naphthyridine-4-carboxylic acid

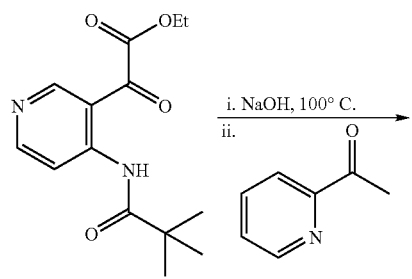

-continued

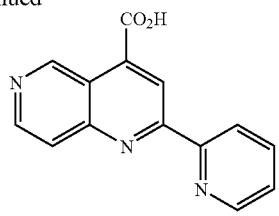

Following the procedure taught in Example 3A, the title compound was prepared having the following characteristics (gray solid, 482 mg, 70%). MS (LR-APCI) calcd. for $C_{14}H_{10}N_3O_2$ (M+H) 252.1; found 252.3.

3M: 2-(3-Methoxy-phenyl)-[1,6]naphthyridine-4-carboxylic acid

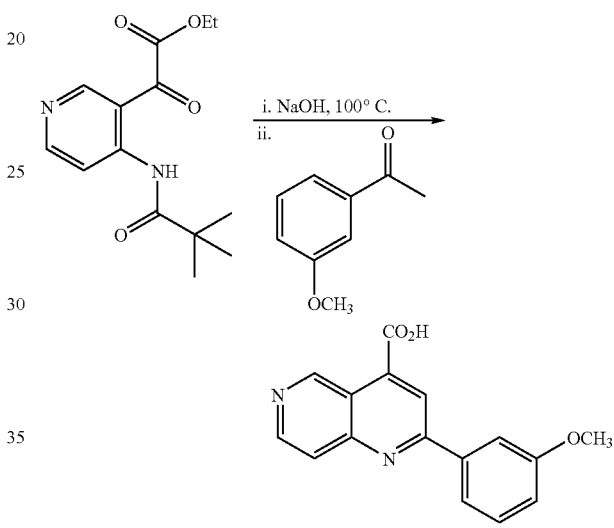

Following the procedure taught in Example 3A, the title compound was prepared having the following characteristics (yellow solid, 548 mg, 72%). MS (LR-APCI) calcd. for $C_{16}H_{13}N_2O_3$ (M+H) 281.1; found 281.4.

3N: 2-Benzo[1,3]dioxol-5-yl-[1,6]naphthyridine-4-carboxylic acid

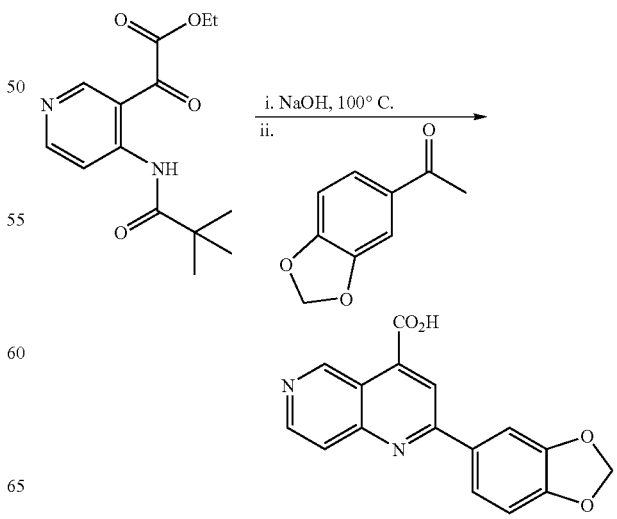

Following the procedure taught in Example 3A, the title compound was prepared having the following characteristics (golden solid, 527 mg, 66%). MS (LR-APCI) calcd. for $C_{16}H_{11}N_2O_4$ (M+H) 295.1; found 295.4.

3O: 2-(3-Chloro-phenyl)-[1,6]naphthyridine-4-carboxylic acid

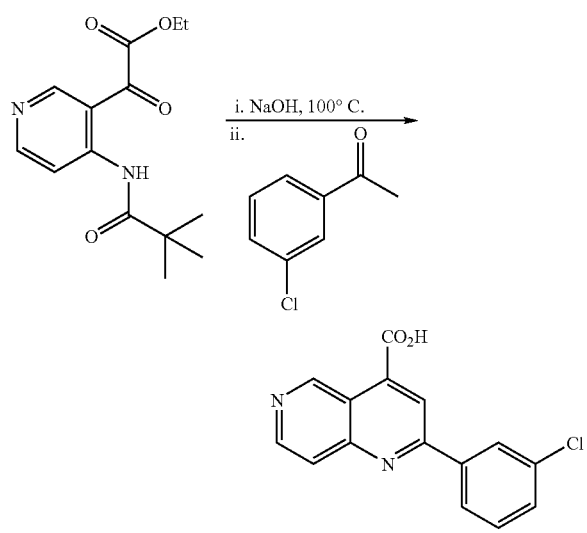

Following the procedure taught in Example 3A, the title compound was prepared having the following characteristics (white solid, 496 mg, 64%). MS (LR-APCI) calcd. for $C_{15}H_{10}ClN_2O_2$ (M+H) 285.0; found 285.6.

3P: 2-m-Tolyl-[1,6]naphthyridine-4-carboxylic acid

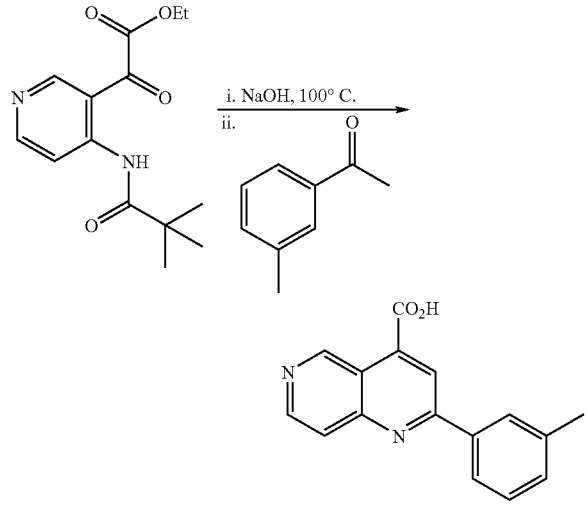

Following the procedure taught in Example 3A, the title compound was prepared having the following characteristics (white solid, 275 mg, 70%). MS (LR-APCI) calcd. for $C_{16}H_{13}N_2O_2$ (M+H) 265.1; found 265.5.

3Q: 2-(3-Trifluoromethyl-phenyl)-[1,6]naphthyridine-4-carboxylic acid

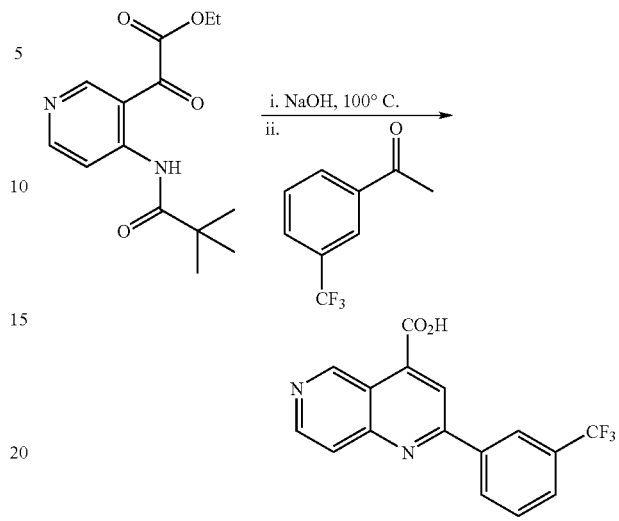

Following the procedure taught in Example 3A, the title compound was prepared having the following characteristics (white solid, 247 mg, 71%). MS (LR-APCI) calcd. for $C_{16}H_{10}F_3N_2O_2$ (M+H) 319.1; found 319.5.

3R: 2-(4-Fluoro-phenyl)-[1,6]naphthyridine-4-carboxylic acid

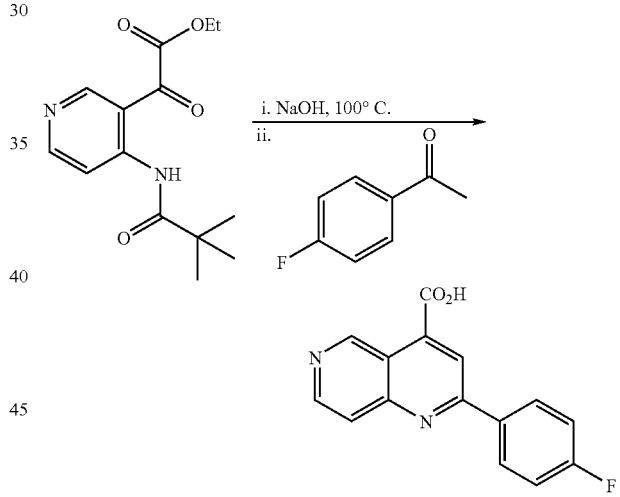

Following the procedure taught in Example 3A, the title compound was prepared having the following characteristics (yellow solid, 200 mg, 68%). MS (LR-APCI) calcd. for $C_{15}H_{10}FN_2O_2$ (M+H) 269.1; found 269.5.

3S: 2-(4-Chloro-phenyl)-[1,6]naphthyridine-4-carboxylic acid

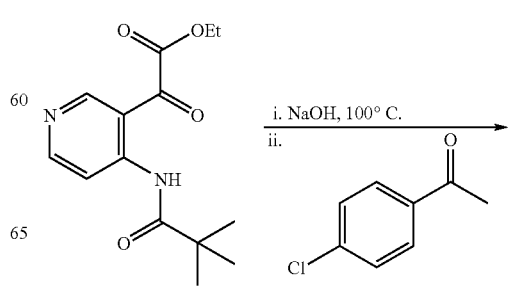

-continued

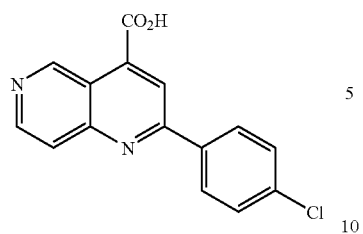

Following the procedure taught in Example 3A, the title compound was prepared having the following characteristics (white solid, 82 mg, 26%). MS (LR-APCI) calcd. for $C_{15}H_{10}ClN_2O_2$ (M+H) 285.0; found 285.5.

3T: 2-(4-Methoxy-phenyl)-[1,6]naphthyridine-4-carboxylic acid

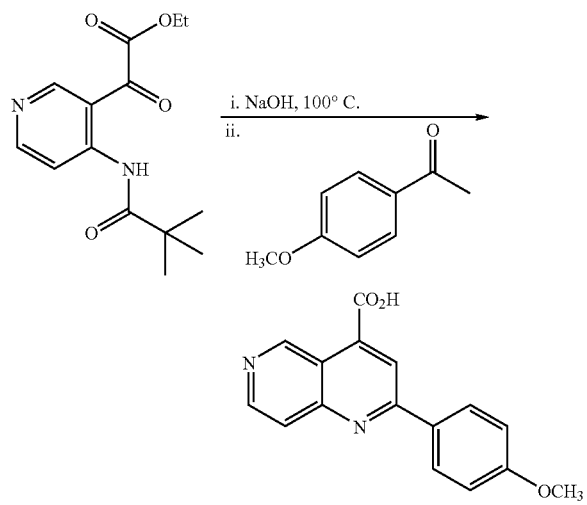

Following the procedure taught in Example 3A, the title compound was prepared having the following characteristics (pale yellow solid, 244 mg, 79%). MS (LR-APCI) calcd. for $C_{16}H_{13}N_2O_3$ (M+H) 281.1; found 281.4.

3U: 2-p-Tolyl-[1,6]naphthyridine-4-carboxylic acid

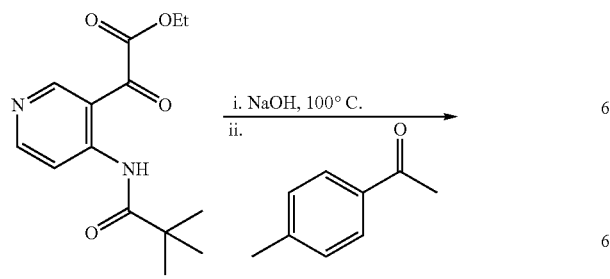

-continued

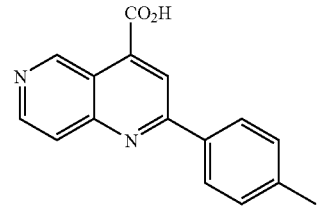

Following the procedure taught in Example 3A, the title compound was prepared having the following characteristics (white solid, 194 mg, 60%). MS (LR-APCI) calcd. for $C_{16}H_{13}N_2O_2$ (M+H) 265.1; found 265.6.

3V: 2-(4-Trifluoromethyl-phenyl)-[1,6]naphthyridine-4-carboxylic acid

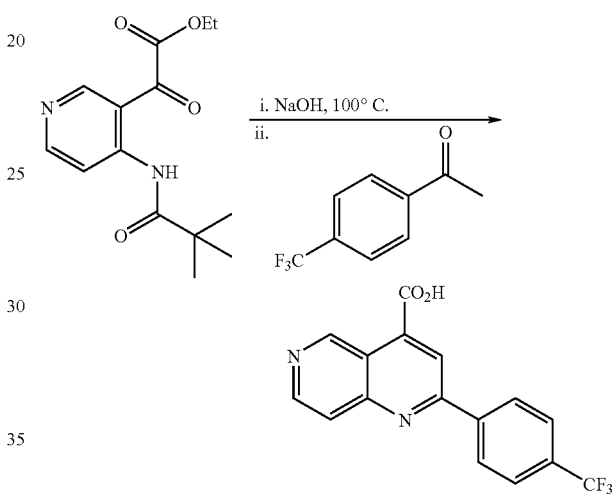

Following the procedure taught in Example 3A, the title compound was prepared having the following characteristics (off-white solid, 270 mg, 69%). MS (LR-APCI) calcd. for $C_{16}H_{10}F_3N_2O_2$ (M+H) 319.1; found 319.6.

3W: 2-(3-Fluoro-phenyl)-[1,6]naphthyridine-4-carboxylic acid

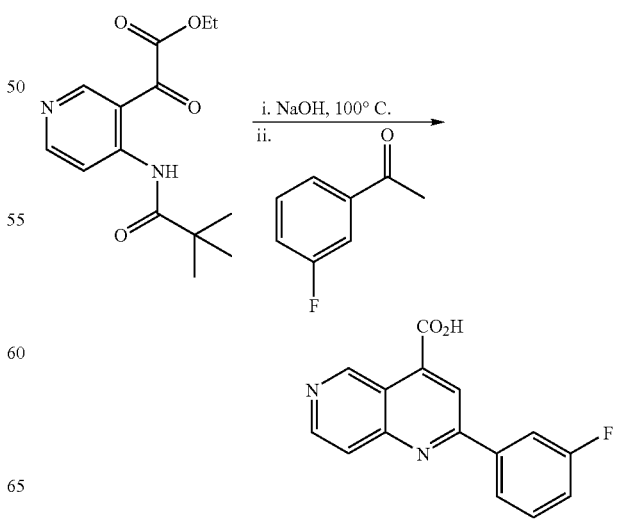

Following the procedure taught in Example 3A, the title compound was prepared having the following characteristics (white solid, 214 mg, 65%). MS (LR-APCI) calcd. for $C_{15}H_{10}FN_2O_2$ (M+H) 269.1; found 269.5.

3X: 2-(2,3-Dihydro-benzo[1,4]dioxin-6-yl)-[1,6]naphthyridine-4-carboxylic acid

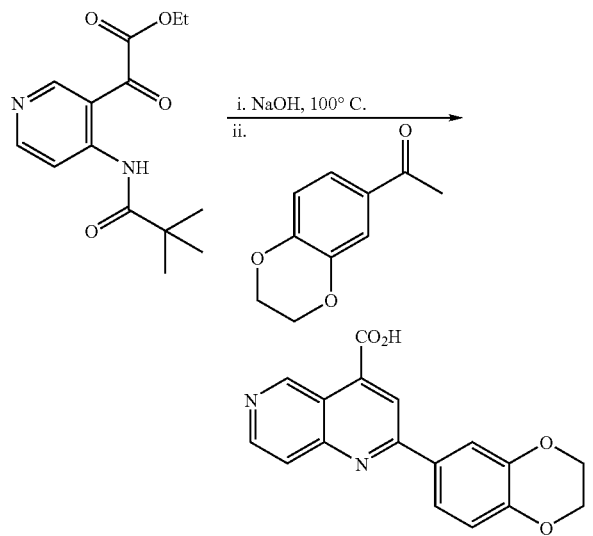

Following the procedure taught in Example 3A, the title compound was prepared having the following characteristics (bright yellow solid, 179 mg, 47%). MS (LR-APCI) calcd. for $C_{17}H_{12}N_2O_4$ (M+H) 309.1; found 309.5.

Example 4

Preparation of 2-Aryl-[1,n]naphthyridin-4-ylamines

4A: 2-Phenyl-[1,8]naphthyridin-4-ylamine

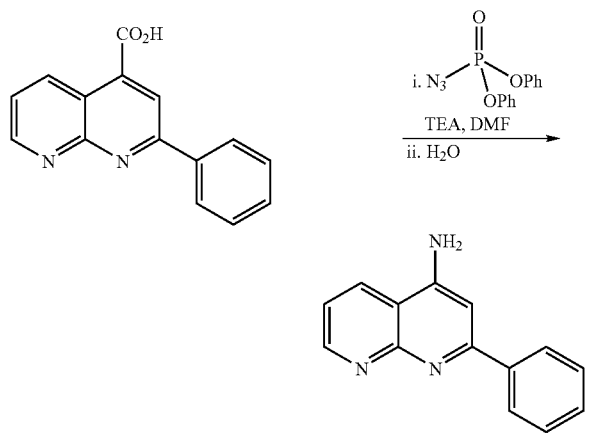

To a solution of 2-phenyl-[1,8]naphthyridine-4-carboxylic acid (549 mg, 1.65 mmol) and triethylamine (0.314 mL, 1.4 equiv) in DMF (to make a ca. 0.2 M solution) was added diphenylphosphoryl azide (0.488 mL, 1.4 equiv) in one portion at ambient temperature and the reaction was stirred for 3 h (note: the solution may become heterogeneous but this will not adversely affect the reaction). Water (add 0.15 mL for each 1.0 mL DMF used) was added and the reaction heated to 100° C. overnight. The reaction was cooled to room temperature and poured into a vigorously stirring mixture of 1N NaOH containing 1% conc. NH$_4$OH. Stirred 15 min and extracted with EtOAc. The organic layer was washed successively with water and brine and was dried (MgSO$_4$). The solution was filtered, concentrated, and taken up in 100 mL EtOAc/Et$_2$O (1:1). Acidification with 2N HCl in Et$_2$O afforded the product as the HCl salt which was collected by vacuum filtration, rinsed with EtOAc, and dried under high vacuum (light yellow solid, 215 mg). $^1$H NMR (400 MHz, DMSO-d$_6$) δ 9.46 (s, 1 H), 9.10-9.07 (m, 1 H), 9.06-9.03 (m, 1 H), 7.90-7.87 (m, 2 H), 7.77 (dd, J=8.6, 4.6 Hz, 1 H), 7.69-7.60 (m, 3 H), 7.08 (s, 1 H). MS (LR-APCI) calcd. for $C_{14}H_{12}N_3$ (M+H) 222.1; found 222.5.

4B: 2-Phenyl-[1,7]naphthyridin-4-ylamine

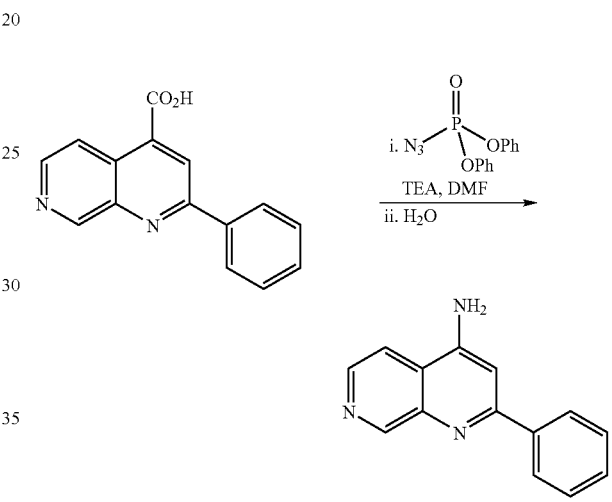

Following the procedure taught in Example 4a, the title compound was prepared, as its HCl salt, having the following characteristics (166 mg). $^1$H NMR (400 MHz, DMSO-d$_6$) δ 9.60 (s, 1 H), 9.46 (br s, 1 H), 8.76 (d, J=6.4 Hz, 1 H), 8.43 (d, J=6.0 Hz, 1 H), 7.99-7.95 (m, 2 H), 7.72-7.65 (m, 3 H), 7.20 (s, 1 H). MS (LR-APCI) calcd. for $C_{14}H_{12}N_3$ (M+H) 222.1; found 222.5.

4C: 2-Phenyl-[1,6]naphthyridin-4-ylamine

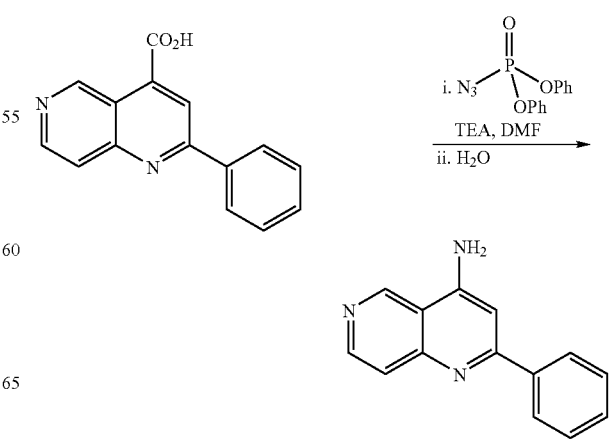

Following the procedure taught in Example 4A, the title compound was prepared, as its TFA salt, followed by preparative reverse phase HPLC. The resultant compound had the following characteristics, $^1$H NMR (400 MHz, DMSO-d$_6$) δ 9.73 (s, 1 H), 9.36 (br s, 2 H), 8.86 (d, J=6.4 Hz, 1 H), 7.93-7.89 (m, 2 H), 7.87 (d, J=6.4 Hz, 1 H), 7.72-7.66 (m, 3 H), 7.09 (s, 1 H). MS (LR-APCI) calcd. for C$_{14}$H$_{12}$N$_3$ (M+H) 222.1; found 222.5.

4D: 2-(3-Chloro-phenyl)-[1,7]naphthyridin-4-ylamine

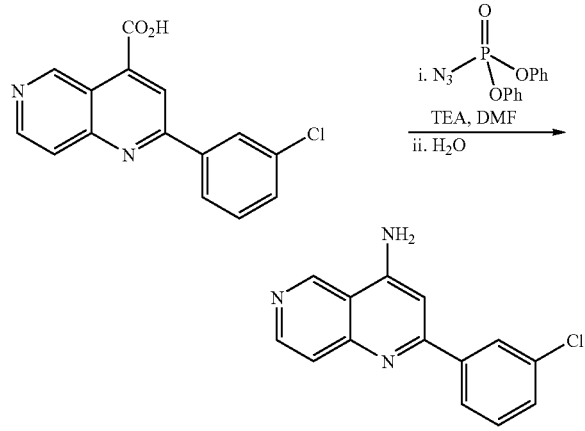

Following the procedure taught in Example 4A, the title compound was prepared, as its HCl salt, having the following characteristics (orange solid, 61 mg). $^1$H NMR (400 MHz, DMSO-d$_6$) δ 9.58 (s, 1 H), 9.46 (br s, 2 H), 8.85-8.79 (m, 1 H), 8.50-8.44 (m, 1 H). 8.13 (s, 1 H), 7.99-7.93 (m, 1 H), 7.85-7.73 (m, 2 H), 7.25 (s, 1 H). MS (LR-APCI) calcd. for C$_{14}$H$_{11}$ClN$_3$ (M+H) 256.1; found 256.3.

4E: 2-Pyridin-2-yl-[1,8]naphthyridin-4-ylamine

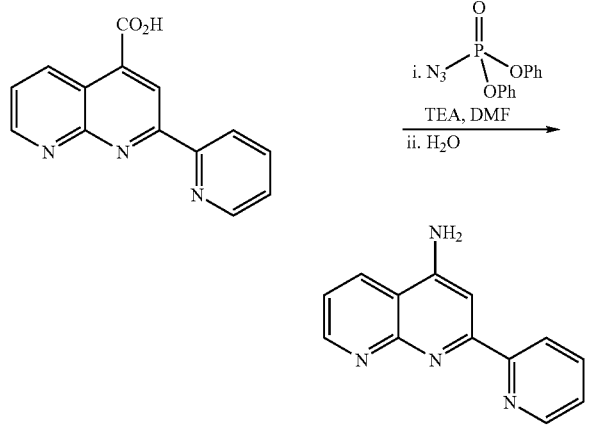

Following the procedure taught in Example 4A, the title compound was prepared, as its HCl salt, having the following characteristics (yellow solid, 57 mg). $^1$H NMR (400 MHz, DMSO-d$_6$) δ 9.55 (br s, 2 H), 9.16-9.13 (m, 1 H), 9.09-9.06 (m, 1 H), 8.90-8.87 (m, 1 H), 8.38 (d, J=7.6 Hz, 1 H), 8.18-8.13 (m, 1 H), 7.82 (dd, J=8.2, 4.2 Hz, 1 H), 7.72 (dd, J=7.8, 4.6 Hz, 1 H), 7.63 (s, 1 H). MS (LR-APCI) calcd. for C$_{13}$H$_{11}$N$_4$ (M+H) 223.1; found 223.2.

4F: 2-(3-Methoxy-phenyl)-[1,8]naphthyridin-4-ylamine

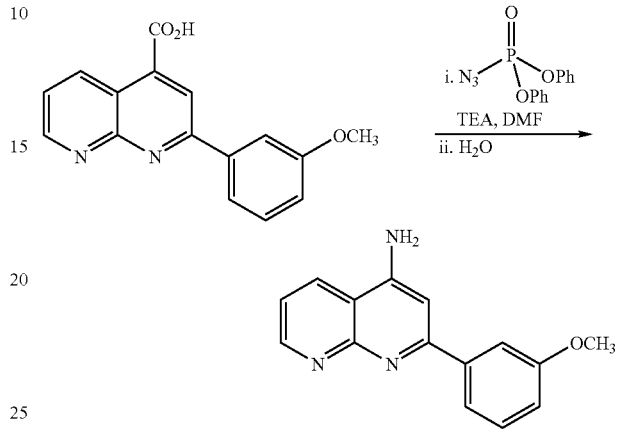

Following the procedure taught in Example 4A, the title compound was prepared, as its HCl salt, having the following characteristics (yellow solid, 210 mg). $^1$H NMR (400 MHz, DMSO-d$_6$) δ 9.46 (br s, 2 H), 9.13-9.10 (m, 1 H), 9.07-9.03 (m, 1 H), 7.80 (dd, J=8.2, 4.2 Hz, 1 H), 7.57 (t, J=7.8 Hz, 1 H), 7.51-7.49 (m, 1 H), 7.46 (d, J=8.0 Hz, 1 H), 7.27-7.23 (m, 1 H), 7.12 (s, 1 H), 3.89 (s, 3 H). MS (LR-APCI) calcd. for C$_{15}$H$_{14}$N$_3$O (M+H) 252.1; found 252.4.

4G: 2-Benzo[1,3]dioxol-5-yl-[1,8]naphthyridin-4-ylamine

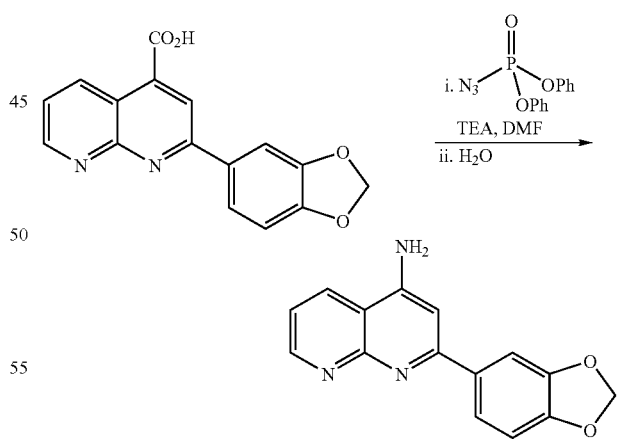

Following the procedure taught in Example 4A, the title compound was prepared, as its HCl salt, having the following characteristics (dark orange solid, 56 mg). $^1$H NMR (400 MHz, DMSO-d$_6$) δ 9.38 (br s, 2 H), 9.10-9.07 (m, 1 H), 9.05-9.02 (m, 1 H), 7.77 (dd, J=8.4, 4.8 Hz, 1 H), 7.52-7.51 (m, 1 H), 7.49-7.45 (m, 1 H), 7.20 (d, J=8.0 Hz, 1 H), 7.06 (s, 1 H), 6.20 (s, 2 H). MS (LR-APCI) calcd. for C$_{15}$H$_{12}$N$_3$O$_2$ (M+H) 266.1; found 266.5.

4H: 2-(3-Chloro-phenyl)-[1,8]naphthyridin-4-ylamine

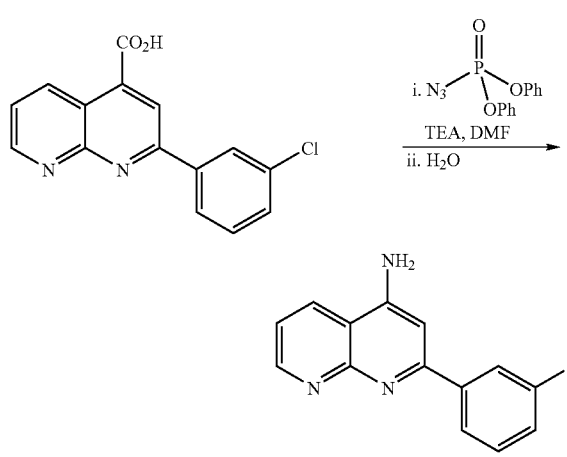

Following the procedure taught in Example 4A, the title compound was prepared, as its HCl salt, having the following characteristics (yellow solid, 203 mg). $^1$H NMR (400 MHz, DMSO-$d_6$) δ 9.46 (br s, 2 H), 9.14-9.12 (m, 1 H), 9.07-9.03 (m, 1 H), 8.02 (s, 1 H), 7.86 (d, J=7.6 Hz, 1 H), 7.81 (dd, J=8.2, 4.2 Hz, 1 H), 7.76 (d, J=7.6 Hz, 1 H), 7.58 (t, J=7.8 Hz, 1 H), 7.09 (s, 1 H). MS (LR-APCI) calcd. for $C_{14}H_{11}ClN_3$ (M+H) 256.1; found 256.3.

4J: 2-(3-Methoxy-phenyl)-[1,6]naphthyridin-4-ylamine

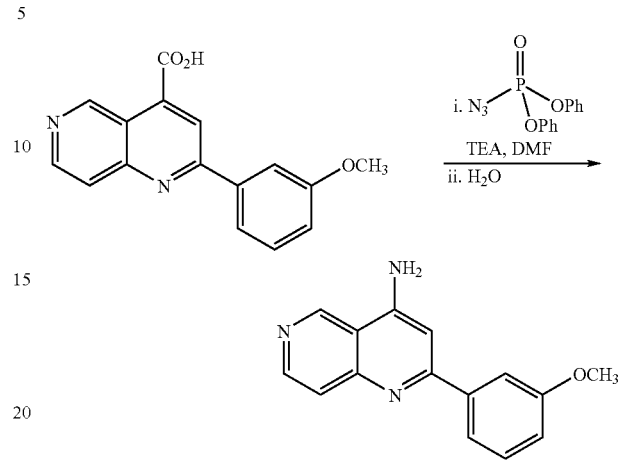

Following the procedure taught in Example 4A, the title compound was prepared, as its HCl salt, having the following characteristics (light orange solid, 211 mg). $^1$H NMR (400 MHz, DMSO-$d_6$) δ 9.83 (s, 1 H), 9.59 (br s, 2 H), 8.88 (d, J=6.4 Hz, 1 H), 8.06 (d, J=6.4 Hz, 1 H), 7.61 (t, J=8.0 Hz, 1 H), 7.54 (s, 1 H), 7.50 (d, J=8.4 Hz, 1 H), 7.31-7.27 (m, 1 H), 7.17 (s, 1 H), 3.90 (s, 3 H). MS (LR-APCI) calcd. for $C_{15}H_{14}N_3O$ (M+H) 252.1; found 252.4.

4I: 2-Pyridin-2-yl-[1,6]naphthyridin-4-ylamine

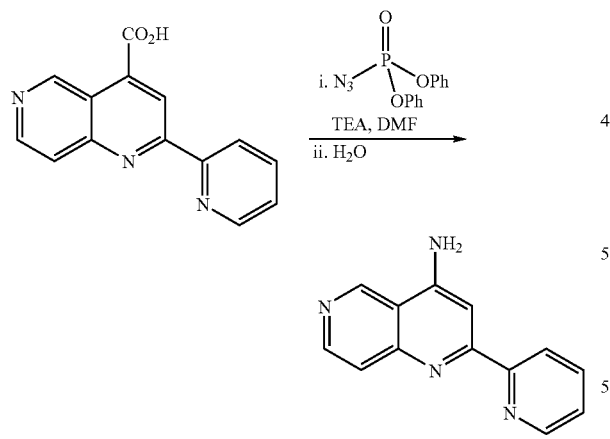

Following the procedure taught in Example 4A, the title compound was prepared, as its HCl salt, having the following characteristics (yellow solid, 65 mg). $^1$H NMR (400 MHz, DMSO-$d_6$) δ 9.90 (s, 1 H), 9.72 (br s, 2 H), 8.93-8.91 (m, 1 H), 8.88 (d, J=6.0 Hz, 1 H), 8.40 (d, J=7.6 Hz, 1 H), 8.24 (d, J=6.0 Hz, 1 H), 8.20 (td, J=7.6, 1.6 Hz, 1 H), 7.78-7.74 (m, 1 H), 7.72 (s, 1 H). MS (LR-APCI) calcd. for $C_{13}H_{11}N_4$ (M+H) 223.1; found 223.3.

4K: 2-Benzo[1,3]dioxol-5-yl-[1,6]naphthyridin-4-ylamine

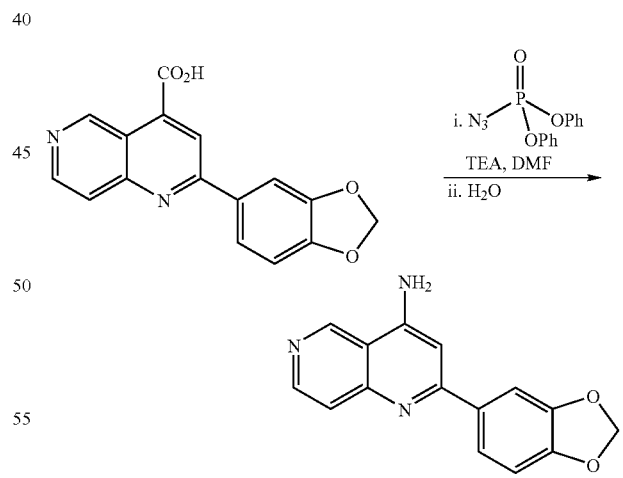

Following the procedure taught in Example 4A, the title compound was prepared, as its HCl salt, having the following characteristics (dark orange solid, 230 mg). $^1$H NMR (400 MHz, DMSO-$d_6$) δ 9.90 (s, 1 H), 9.62 (br s, 2 H), 8.87 (d, J=5.2 Hz, 1 H), 8.16 (d, J=6.4 Hz, 1 H), 7.61 (s, 1 H), 7.56 (d, J=8.8 Hz, 1 H), 7.23 (d, J=7.6 Hz, 1 H), 7.17 (s, 1 H), 6.22 (s, 2 H). MS (LR-APCI) calcd. for $C_{15}H_{12}N_3O_2$ (M+H) 266.1; found 266.4.

37

4L: 2-(3-Chloro-phenyl)-[1,6]naphthyridin-4-ylamine

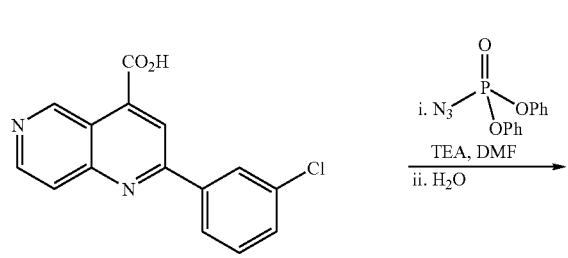

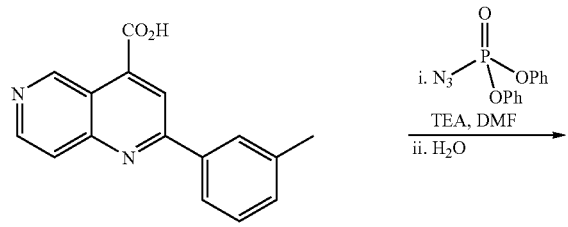

Following the procedure taught in Example 4A, the title compound was prepared, as its HCl salt, having the following characteristics (light orange solid, 255 mg). $^1$H NMR (400 MHz, DMSO-$d_6$) δ 9.88 (s, 1 H), 9.57 (br s, 2 H), 8.91-8.85 (m, 1 H), 8.09 (s, 1 H), 8.08-8.02 (m, 1 H), 7.97-7.90 (1 H), 7.81-7.68 (m, 2 H), 7.21 (s, 1 H). MS (LR-APCI) calcd. for $C_{14}H_{11}ClN_3$ (M+H) 256.1; found 256.5.

4M: 2-m-Tolyl-[1,6]naphthyridin-4-ylamine

Following the procedure taught in Example 4A, the title compound was prepared, as its HCl salt, having the following characteristics. $^1$H NMR (400 MHz, DMSO-$d_6$) δ 9.86 (s, 1 H), 9.62 (br s, 2 H), 8.88 (d, J=5.2 Hz, 1 H), 8.06 (d, J=6.0 Hz, 1 H), 7.80 (s, 1 H), 7.75 (d, J=8.0 Hz, 1 H), 7.58 (t, J=7.2 Hz, 1 H), 7.54 (d, J=8.0 Hz, 1 H), 7.17 (s, 1 H), 2.46 (s, 3 H). MS (LR-APCI) calcd. for $C_{15}H_{14}N_3$ (M+H) 236.1; found 236.6.

38

4N: 2-(3-Trifluoromethyl-phenyl)-[1,6]naphthyridin-4-ylamine

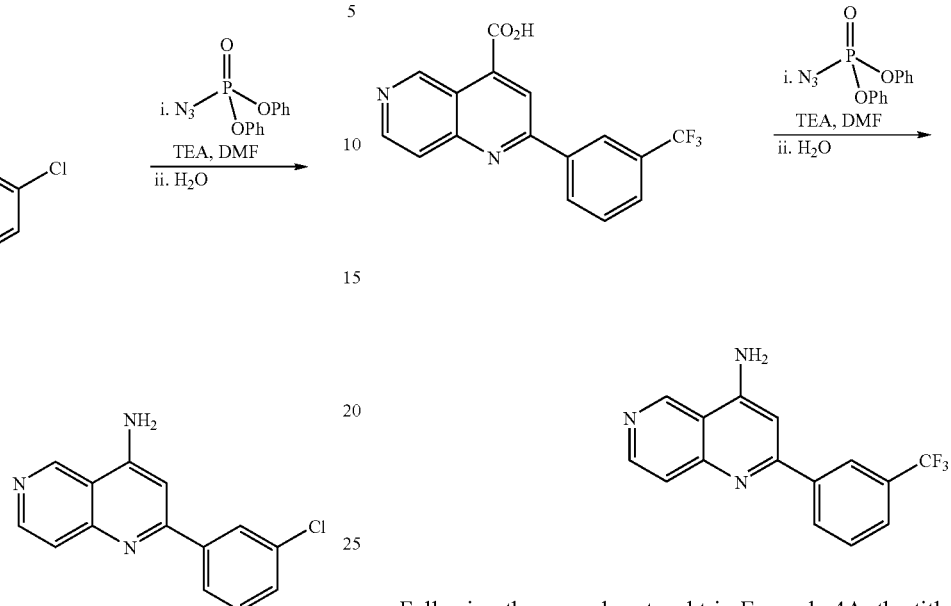

Following the procedure taught in Example 4A, the title compound was prepared, as its HCl salt, having the following characteristics (245 mg). $^1$H NMR (400 MHz, DMSO-$d_6$) δ 9.90 (s, 1 H), 9.51 (br s, 2 H), 8.88 (d, J=6.0 Hz, 1 H), 8.36 (s, 1 H), 8.29 (d, J=8.0 Hz, 1 H), 8.10-8.04 (m, 2 H), 7.92 (t, J=7.8 Hz, 1 H), 7.26 (s, 1 H). MS (LR-APCI) calcd. for $C_{15}H_{11}F_3N_3$ (M+H) 290.1; found 290.6.

4O: 2-(4-Fluoro-phenyl)-[1,6]naphthyridin-4-ylamine

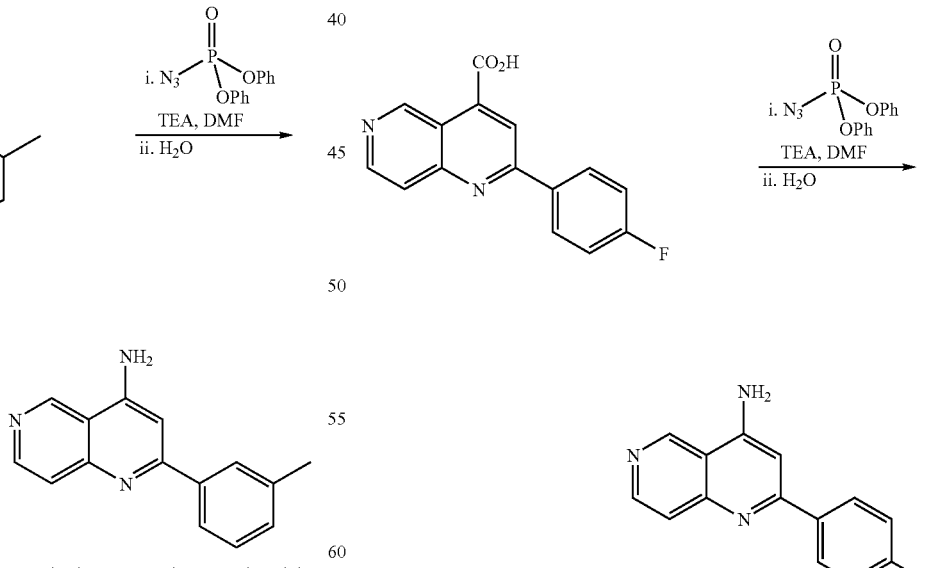

Following the procedure taught in Example 4A, the title compound was prepared, as its HCl salt, having the following characteristics (163 mg). $^1$H NMR (400 MHz, DMSO-$d_6$) δ 9.86 (s, 1 H), 9.57 (br s, 2 H), 8.87 (d, J=5.6 Hz, 1 H), 8.08-8.03 (m, 3 H), 7.56 (t, J=9.2 Hz, 2 H), 7.16 (s, 1 H). MS (LR-APCI) calcd. for $C_{14}H_{11}FN_3$ (M+H) 240.1; found 240.2.

4P: 2-(4-Chloro-phenyl)-[1,6]naphthyridin-4-ylamine

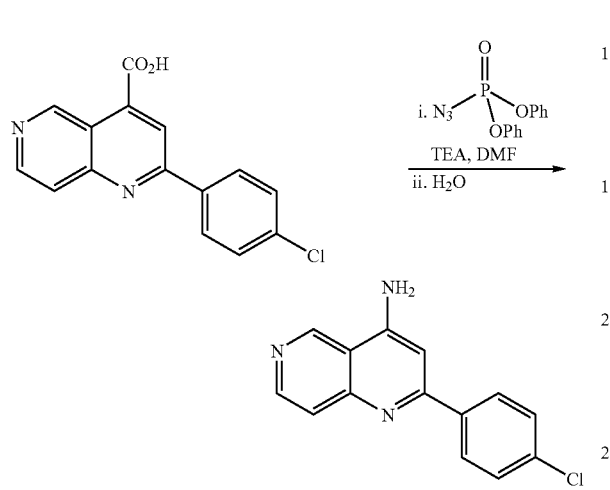

Following the procedure taught in Example 4A, the title compound was prepared, as its HCl salt, having the following characteristics (23 mg). $^1$H NMR (400 MHz, DMSO-$d_6$) δ 9.87 (s, 1 H), 9.58 (br s, 2 H), 8.87 (d, J=5.2 Hz, 1 H), 8.06 (d, J=5.2 Hz, 1 H), 8.01 (d, J=8.4 Hz, 2 H), 7.78 (d, J=8.4 Hz, 2 H), 7.18 (s, 1 H). MS (LR-APCI) calcd. for $C_{14}H_{11}ClN_3$ (M+H) 256.1; found 256.5.

4Q: 2-(4-Methoxy-phenyl)-[1,6]naphthyridin-4-ylamine

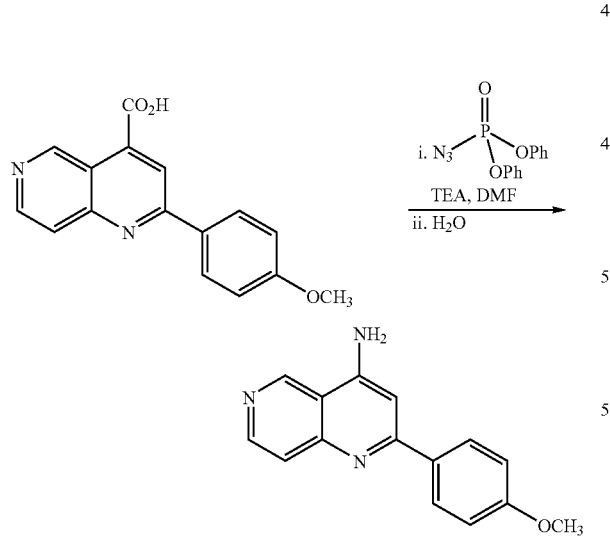

Following the procedure taught in Example 4A, the title compound was prepared, as its HCl salt, having the following characteristics (154 mg). $^1$H NMR (400 MHz, DMSO-$d_6$) δ 9.91 (s, 1 H), 9.65 (br s, 2 H), 8.87 (d, J=6.0 Hz, 1 H), 8.20 (d, J=6.4 Hz, 1 H), 8.01 (d, J=9.6 Hz, 2 H), 7.24 (d, J=8.8 Hz, 2 H), 7.21 (s, 1 H), 3.90 (s, 3 H). MS (LR-APCI) calcd. for $C_{15}H_{14}N_3O$ (M+H) 252.1; found 252.4.

4R: 2-p-Tolyl-[1,6]naphthyridin-4-ylamine

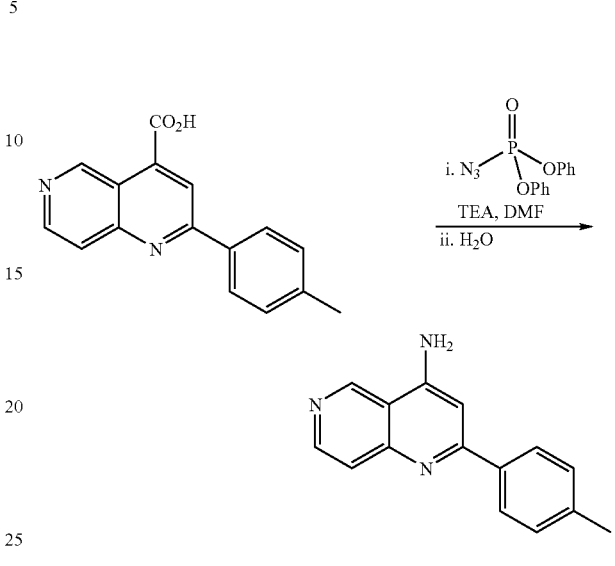

Following the procedure taught in Example 4A, the title compound was prepared, as its HCl salt, having the following characteristics (dirty pale yellow solid, 136 mg). $^1$H NMR (400 MHz, DMSO-$d_6$) δ 9.92 (s, 1 H), 9.71 (br s, 2 H), 8.88 (d, J=6.4 Hz, 1 H), 8.18 (d, J=6.4 Hz, 1 H), 7.91 (d, J=8.0 Hz, 2 H), 7.50 (d, J=8.8 Hz, 2 H), 7.22 (s, 1 H), 2.44 (s, 3 H). MS (LR-APCI) calcd. for $C_{15}H_{14}N_3$ (M+H) 236.1; found 236.6.

4S: 2-(4-Trifluoromethyl-phenyl)-[1,6]naphthyridin-4-ylamine

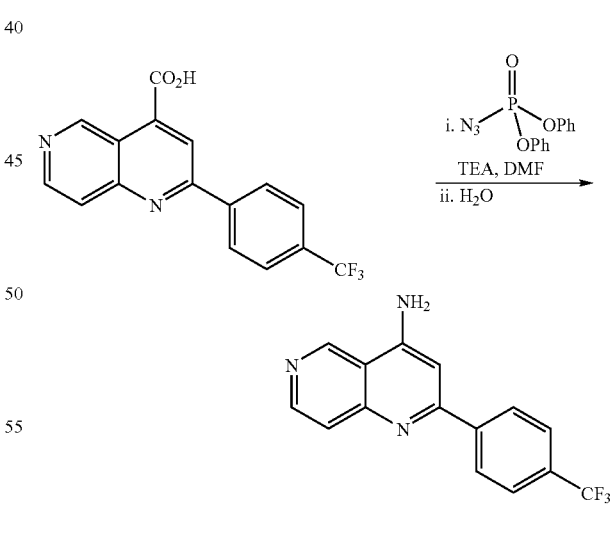

Following the procedure taught in Example 4A, the title compound was prepared, as its HCl salt, having the following characteristics (tan solid, 158 mg). $^1$H NMR (400 MHz, DMSO-$d_6$) δ 9.99 (s, 1 H), 9.76 (br s, 2 H), 8.88 (d, J=6.4 Hz, 1 H), 8.24-8.18 (m, 3 H), 8.06 (d, J=8.4 Hz, 2 H), 7.29 (s, 1 H). MS (LR-APCI) calcd. for $C_{15}H_{11}F_3N_3$ (M+H) 290.1; found 290.6.

4T: 2-(3-Fluoro-phenyl)-[1,6]naphthyridin-4-ylamine

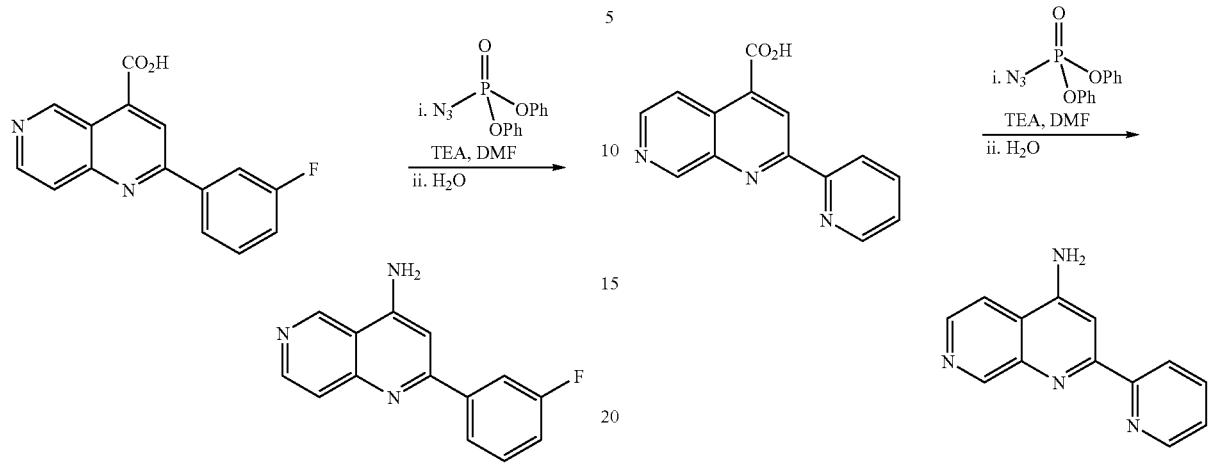

Following the procedure taught in Example 4A, the title compound was prepared as its HCl salt. The crude HCl salt was further purified by C18 chromatography to obtain the product as its free base having the following characteristics (bright yellow solid, 71 mg). $^1$H NMR (400 MHz, DMSO-$d_6$) δ 9.89 (s, 1 H), 9.62 (br s, 2 H), 8.84 (d, J=6.0 Hz, 1 H), 8.12 (d, J=5.2 Hz, 1 H), 7.91 (d, J=10.0 Hz, 1 H), 7.84 (d, J=7.6 Hz, 1 H), 7.74-7.68 (m, 1 H), 7.54 (td, J=8.2, 1.6 Hz, 1 H), 7.27 (s, 1 H). MS (LR-APCI) calcd. for $C_{14}H_{11}FN_3$ (M+H) 240.1; found 240.5.

4U: 2-(2,3-Dihydro-benzo[1,4]dioxin-6-yl)-[1,6]naphthyridin-4-ylamine

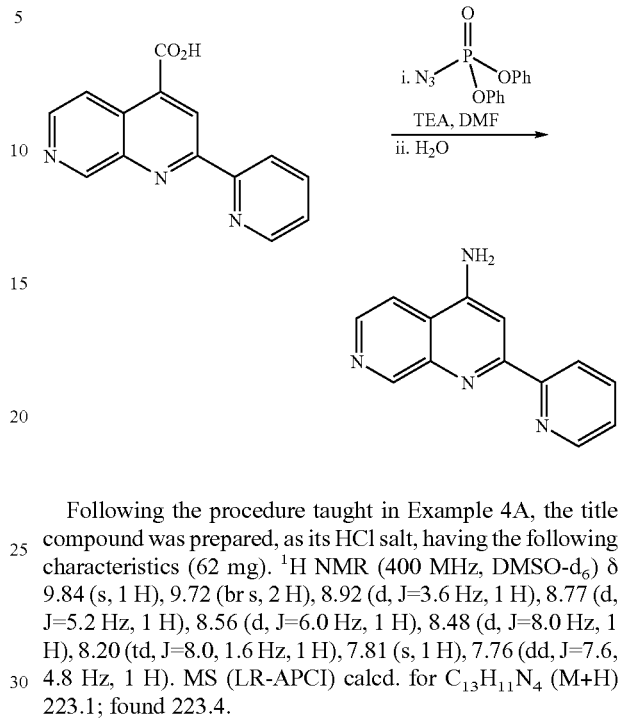

Following the procedure taught in Example 4A, the title compound was prepared, as its HCl salt, having the following characteristics (yellow solid, 170 mg). $^1$H NMR (400 MHz, DMSO-$d_6$) δ 9.90 (s, 1 H), 9.65 (br s, 2 H), 8.87 (d, J=6.4 Hz, 1 H), 8.16 (d, J=6.4 Hz, 1 H), 7.59 (d, J=2.4 Hz, 1 H), 7.51 (dd, J=8.8, 1.6 Hz, 1 H), 7.19 (s, 1 H), 7.16 (d, J=8.8 Hz, 1 H), 4.37 (dd, J=10.0, 5.2 Hz, 4 H). MS (LR-APCI) calcd. for $C_{16}H_{14}N_3O_2$ (M+H) 280.1; found 280.4.

4V: 2-Pyridin-2-yl-[1,7]naphthyridin-4-ylamine

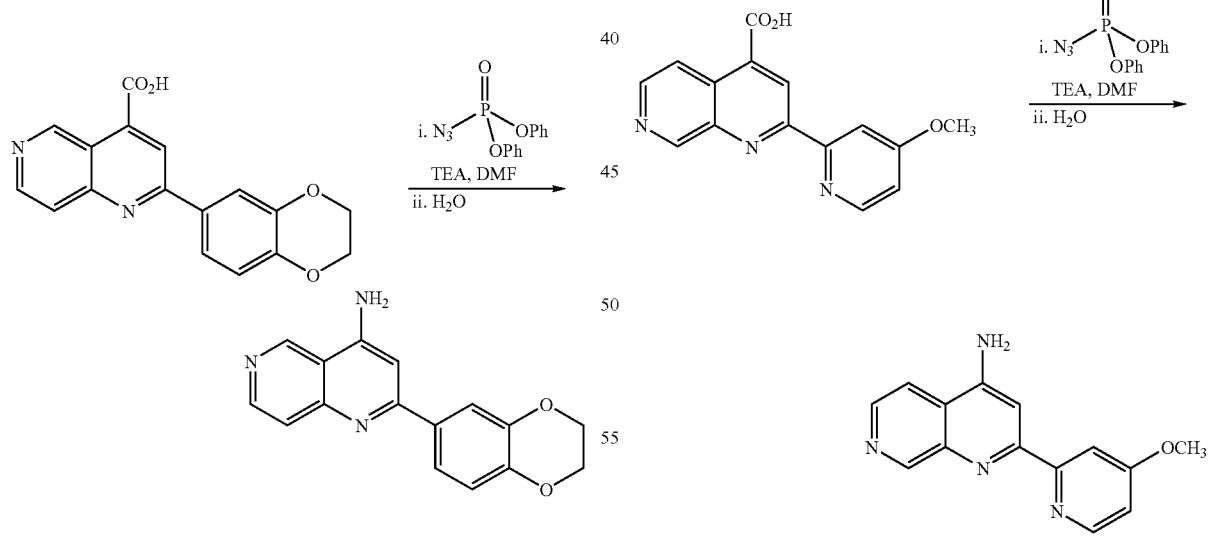

Following the procedure taught in Example 4A, the title compound was prepared, as its HCl salt, having the following characteristics (62 mg). $^1$H NMR (400 MHz, DMSO-$d_6$) δ 9.84 (s, 1 H), 9.72 (br s, 2 H), 8.92 (d, J=3.6 Hz, 1 H), 8.77 (d, J=5.2 Hz, 1 H), 8.56 (d, J=6.0 Hz, 1 H), 8.48 (d, J=8.0 Hz, 1 H), 8.20 (td, J=8.0, 1.6 Hz, 1 H), 7.81 (s, 1 H), 7.76 (dd, J=7.6, 4.8 Hz, 1 H). MS (LR-APCI) calcd. for $C_{13}H_{11}N_4$ (M+H) 223.1; found 223.4.

4W: 2-(3-Methoxy-phenyl)-[1,7]naphthyridin-4-ylamine

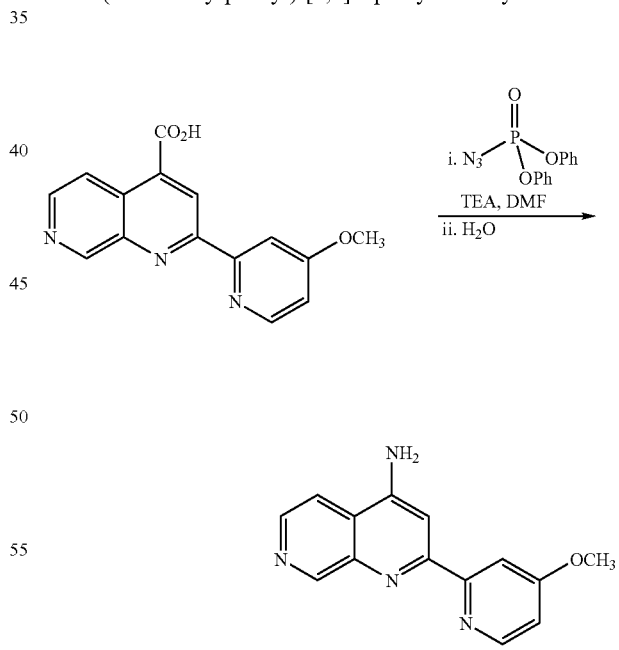

Following the procedure taught in Example 4A, the title compound was prepared, as its HCl salt, having the following characteristics (65 mg). $^1$H NMR (400 MHz, DMSO-$d_6$) δ 9.75 (s, 1 H), 9.55 (br s, 2 H), 8.77 (d, J=5.2 Hz, 1 H), 8.49 (d, J=6.0 Hz, 1 H), 7.62 (s, 1 H), 7.59 (d, J=7.6 Hz, 1 H), 7.53 (d, J=7.6 Hz, 1 H), 7.29-7.25 (m, 2 H), 3.92 (s, 3 H). MS (LR-APCI) calcd. for $C_{15}H_{14}N_3O$ (M+H) 252.1; found 252.4.

4X: 2-Benzo[1,3]dioxol-5-yl-[1,7]naphthyridin-4-ylamine

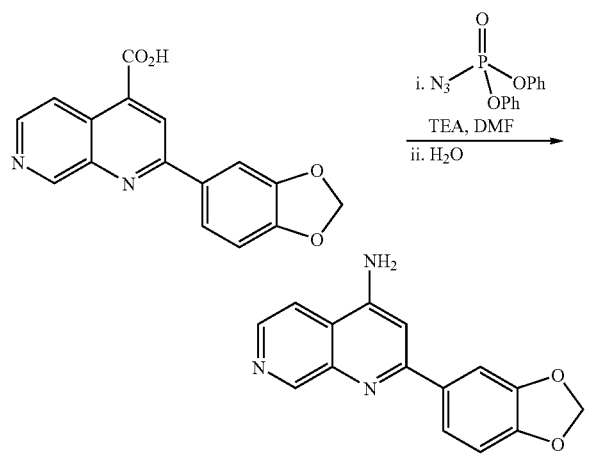

Following the procedure taught in Example 4A, the title compound was prepared, as its TFA salt. The TFA salt was further purified by preparative reverse phase HPLC, yielding a compound having the following characteristics. $^1$H NMR (400 MHz, DMSO-$d_6$) δ 9.39 (s, 1 H), 9.01 (br s, 2 H), 8.74 (d, J=6.4 Hz, 1 H), 8.30 (d, J=5.6 Hz, 1 H), 7.56 (d, J=1.6 Hz, 1 H), 7.53-7.50 (m, 1 H), 7.24 (d, J=7.6 Hz, 1 H), 7.11 (s, 1 H), 6.21 (s, 2 H). MS (LR-APCI) calcd. for $C_{15}H_{12}N_3O_2$ (M+H) 266.1; found 266.5.

Example 5

Functional Mobilization of Intracellular Calcium to Determine Muscarinic Receptor Activity CHO cells expressing muscarinic receptors ($M_1$ to M5) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat# 12430-054), containing 25 mM Hepes and supplemented with Fetal Bovine Serum (Hyclone, cat# SH30071.03), 0.1 mM of MEM non-essential amino acids (GIBCO, Cat# 11140-050), 1 mM MEM Sodium Pyruvate (GIBCO Cat# 11360-070) and 100 units/ml of Penicillin G and 100 μg/ml of Streptomycin (GIBCO Cat# 15140-122). The recombinant muscarinic receptor cell lines are grown under antibiotic pressure with media containing 25 μg/ml zeocin and 500 μg/ml G418 (M1-CHO), 4 μg/ml puromycin, 50 μg/ml zeocin and 2.5 μg/ml blasticidin (M2 and M4-CHO) or 50 μg/ml zeocin and 4 μg/ml puromycin (M3 and M5-CHO).

Cells are harvested at 80-90% confluence using Versene (GIBCO Cat# 15040-066), collected by centrifugation and seeded 18-24 hrs prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using bath1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 μl/well of Fluo-3 AM at 4 μM, Molecular Probes F-1241, in Bath 1 buffer containing 1 mM Probenecid) is added to the 25 μl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 μl/well of this solution after the wash. Alternatively, cells can be loaded with the calcium indicator from Molecular Devices (Calcium 3 Assay Reagents, Cat # R7181) adding 5 μl of a 5× solution dye in Bath 1 containing 1 mM Probenecid (10 ml per dye flask cat# R7182 to generate a solution 20×) to 20 μl of the same buffer. After loading for 60 min, the experiment can be run without having to remove the dye.

Compounds are prepared at a 2× fold concentration in a 96-well plate (round bottom, Costar Corning cat# 3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 μl compound/well) to the cell assay plate (containing 25 μl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 μl compound/well) to the assay plate and pre-incubated for 15 min prior to adding 25 μl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to M5 cells).

The compounds of the present invention were found to selectively modulate the muscarinic receptors selectively over the other receptor types.

Example 6

β-Lactamase Assay to Determine Muscarinic Receptor Activity

CHO cells expressing muscarinic receptors ($M_1$ to M5) and containing a gene reporter system (β-Lactamase) with transcriptional control mediated by calcium release (NFAT activation). See Zlokarnik, G; Negulescu, P. A.; Knapp, T. E.; Mere, L; Burres, N; Feng, L; Whitney, M; Roemer, K; Tsien, R. Y. Quantitation of transcription and clonal selection of single living cells with β-lactamase as reporter. Science, 1998 Jan. 2, 279(5347):84-8. The cells are grown as monolayers in tissue culture flasks at 37° C. in a humidified atmosphere containing 5% $CO_2$ and passaged every 3-5 days. The growth media is Dulbecco's modified eagles medium (DMEM, Gibco Cat# 12430-054), containing 25 mM Hepes and supplemented with 10% Fetal Bovine Serum (Hyclone, cat# SH30071.03), 0.1 mM of MEM non-essential amino acids (GIBCO, Cat# 11140-050), 1 mM MEM Sodium Pyruvate (GIBCO Cat# 11360-070) and 100 units/ml of Penicillin G and 100 μg/ml of Streptomycin (GIBCO Cat# 15140-122). The recombinant muscarinic receptor cell lines are grown under antibiotic pressure with media containing 25 μg/ml zeocin and 500 μg/ml G418 (M1-CHO), 4 μg/ml puromycin, 50 μg/ml zeocin and 2.5 μg/ml blasticidin (M2 and M4-CHO) or 50 μg/ml zeocin and 4 μg/ml puromycin (M3 and M5-CHO).

Cells are harvested at 80-90% confluence using Accutase (Innovative Cell Technologies, Inc. Cat# AT104), collected by centrifugation and seeded for 2-6 hours at a density of 15,000-20,000 cells/well in black-walled, clear-bottomed 384-well plates (BD Biocoat, poly-D-lysine, Cat#356663). Media is replaced with DMEM +1% Fetal Bovine Serum and incubated for another 12-18 hrs prior to running the β-Lactamase assay. The day of the experiment, compounds are prepared at a 1× fold concentration in a 96-well plate (round bottom, Costar Corning cat#3656), by reconstituting the pre-spotted compounds in DMEM +1% FBS. The final concentration of DMSO is 0.5%, and the amount of DMSO is normalized across the assay plate. To determine an agonist action of the compounds on muscarinic receptors, the reconstituted compounds are added (25 μl compound/well) to the cell assay plate (where the media has been removed) using the multichannel robotic system, Multimek 96 (Beckman). The compounds are incubated with the cells for 3 hours at 37° C., 5% $CO_2$. to allow for expression of the reporter gene β-Lactamase.

After 3 hours, 5 μl of 6× fold concentrated CCF2/AM dye are added to the assay plates and incubated at room temperature for 1 hour. Fluorescent emission at two wavelengths (460 nm and 530 nm) is determined using the CytoFluor Series 4000 (PerSeptive Biosystems) and the calculations for reporter gene expression determined as specified in prior publications {Zlokamik, G; Negulescu, P. A.; Knapp, T. E.; Mere, L; Burres, N; Feng, L; Whitney, M; Roemer, K; Tsien, R. Y. Quantitation of transcription and clonal selection of single living cells with β-lactamase as reporter. Science, Jan 2, 1998 279(5347):84-8.}

The compounds of the present invention were found to modulate the muscarinic receptor activity using the β-Lactamase Assay.

What is claimed:

1. A compound of Formula I,

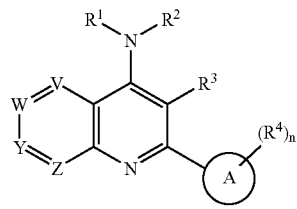

I wherein:
Ring A is phenyl, pyridine-2-yl, benzodioxol, or benzodioxine;
W is nitrogen and each of V, Y and Z is —C($R^5$)—;
Each $R^1$ is independently selected from H, aliphatic, cycloaliphatic, heteroaliphatic and heterocycle, wherein each of the aliphatic, cycloaliphatic, heteroaliphatic and heterocycle is optionally substituted with 1-3 Ra;
Each $R^2$ is independently selected from H, aryl, heteroaryl, aliphatic, cycloaliphatic, heteroaliphatic, heterocycle, —C(O)Rc, and —S(O)$_2$Rc, wherein each aliphatic, cycloaliphatic, heteroaliphatic and heterocycle is optionally substituted with 1-3 Ra, and wherein each aryl and heteroaryl is optionally substituted with 1-3 Rb,
Each $R^3$ is independently H, halo, haloaliphatic, aliphatic, —ORd, or —S(O)$_i$Rd;
Each $R^4$ is independently selected from H, halogen, —CN, —OH, —NO$_2$, —ORd, —C(O)Rd, —C(O)ORd, —C(O)N(Rd)$_2$, —N(Rd)$_2$, —N(Rd)C(O)Rd, —N(Rd)C(O)ORd, —OC(O)ORd, —OC(O)NRd, —N(Rd)S(O)$_2$ Rd, aliphatic optionally substituted with 1-3 Ra, and any two adjacent $R^4$ on Ring A together with the atoms to which they are attached may be taken together to form a heterocyclic or carbocyclic ring;
Each $R^5$ is independently selected from H, halogen, —CN, —OH, —NO$_2$, —ORd, —C(O)Rd, —C(O)ORd, —C(O)N(Rd)$_2$, —N(Rd)$_2$, —N(Rd)C(O)Rd, —N(Rd)C(O)ORd, —OC(O)ORd, —OC(O)NRd, —N(Rd)S(O)$_2$ Rd, aliphatic optionally substituted with 1-3 of Ra, and any two adjacent $R^5$ together with the atoms to which they are attached may be taken together to form a heterocyclic or carbocyclic ring;
Each Ra is independently selected from aryl, heteroaryl, halogen, —CN, —OH, —ORd, —C(O)Rd, —C(O)ORd, —C(O)N(Rd)$_2$, —N(Rd)$_2$, —NRdC(O)Rd, —N(Rd)C(O)ORd, —N(Rd)C(O)N(Rd)$_2$, —OC(O)ORd, —OC(O)N(Rd)$_2$, =N—OH, =NORd, =N=N(Rd)$_2$, =O, =S, —S(O)$_2$N(Rd)$_2$, —N(Rd)S(O)$_2$Rd, —N(Rd)S(O)$_i$N(Rd)$_2$ and —S(O)$_i$Rd;
Each Rb is independently selected from halo, aryl, —OH, —ORd, —S(O)$_i$Rd, —N(Rd)$_2$, —NRdC(O)Rd, —NRdC(O)ORd, —C(O)Rd, —C(O)ORd, —C(O)N(Rd)$_2$, —S(O)$_i$N(Rd)$_2$, —CN, and —NO$_2$;
Each Rc is independently selected from H, aliphatic, cycloaliphatic, heteroaliphatic, heterocycle, aryl, heteroaryl, —ORd, and —N(Rd)$_2$, wherein the aliphatic, cycloaliphatic, heteroaliphatic, heterocycle, aryl, and heteroaryl are optionally substituted with 1-3 of Ra;
Each Rd is independently selected from H, aliphatic, heteroaliphatic, heterocycle, cycloaliphatic, aryl, heteroaryl, wherein each of aliphatic, heteroaliphatic, heterocycle, cycloaliphatic, aryl, heteroaryl may be optionally substituted with 1-3 of halo, aryl, —OH, —Oaliphatic, —Oaryl, —Oacyl, —NH$_2$, —N(aliphatic)$_2$, —N(aryl)$_2$, —S(O)$_i$aliphatic, or —S(O)$_i$aryl;
n is 0 to 3; and
i is 0 to 2.

2. The compound of claim 1, wherein one of $R^1$ and $R^2$ is H.
3. The compound of claim 2, wherein both of $R^1$ and $R^2$ are H.
4. The compound of claim 2, wherein A is phenyl.
5. The compound of claim 3, wherein $R^4$ is selected from the group consisting of halogen, —ORd, and aliphatic optionally substituted with 1-3 of Ra.
6. The compound of claim 5, wherein $R^4$ is —Oaliphatic or haloaliphatic.
7. A compound selected from the group consisting of
2-Phenyl-[1,6]naphthyridin-4-ylamine,
2-(3-Methoxy-phenyl)-[1,6]naphthyridin-4-ylamine,
2-Benzo[1,3]dioxol-5-yl-[1,6]naphthyridin-4-ylamine,
2-(3-Chloro-phenyl)-[1,6]naphthyridin-4-ylamine,
2-m-Tolyl-[1,6]naphthyridin-4-ylamine,
2-(3-Trifluoromethyl-phenyl)-[1,6]naphthyridin-4-ylamine,
2-(4-Fluoro-phenyl)-[1,6]naphthyridin-4-ylamine,
2-(4-Chloro-phenyl)-[1,6]naphthyridin-4-ylamine,
2-(4-Methoxy-phenyl)-[1,6]naphthyridin-4-ylamine,
2-p-Tolyl-[1,6]naphthyridin-4-ylamine,
2-(4-Trifluoromethyl-phenyl)-[1,6]naphthyridin-4-ylamine,
2-(3-Fluoro-phenyl)-[1,6]naphthyridin-4-ylamine, and
2-(2,3-Dihydro-benzo[1,4]dioxin-6-yl)-[1,6]naphthyridin-4-ylamine.

8. A pharmaceutical composition comprising a compound a compound according to claim 1 and a pharmaceutical carrier.

* * * * *

UNITED STATES PATENT AND TRADEMARK OFFICE
CERTIFICATE OF CORRECTION

| | |
|---|---|
| PATENT NO. | : 7,446,112 B2 |
| APPLICATION NO. | : 11/005944 |
| DATED | : November 4, 2008 |
| INVENTOR(S) | : Peter D. J. Grootenhuis et al. |

Page 1 of 1

It is certified that error appears in the above-identified patent and that said Letters Patent is hereby corrected as shown below:

In column 46, line 62, please delete a single occurrence of "a compound".

Signed and Sealed this

Twenty-seventh Day of January, 2009

JOHN DOLL
*Acting Director of the United States Patent and Trademark Office*